(12) United States Patent
Cao et al.

(10) Patent No.: US 11,454,591 B2
(45) Date of Patent: Sep. 27, 2022

(54) BIOSENSOR

(71) Applicant: Shenzhen Genorivision Technology Co., Ltd., Shenzhen (CN)

(72) Inventors: Peiyan Cao, Shenzhen (CN); Yurun Liu, Shenzhen (CN)

(73) Assignee: SHENZHEN GENORIVISION TECHNOLOGY CO., LTD., Shenzhen (CN)

( * ) Notice: Subject to any disclaimer, the term of this patent is extended or adjusted under 35 U.S.C. 154(b) by 680 days.

(21) Appl. No.: 15/737,812

(22) PCT Filed: Dec. 7, 2015

(86) PCT No.: PCT/CN2015/096539
§ 371 (c)(1),
(2) Date: Dec. 19, 2017

(87) PCT Pub. No.: WO2017/096504
PCT Pub. Date: Jun. 15, 2017

(65) Prior Publication Data
US 2019/0003971 A1    Jan. 3, 2019

(51) Int. Cl.
*G01N 21/00* (2006.01)
*G01N 21/64* (2006.01)
(Continued)

(52) U.S. Cl.
CPC .... *G01N 21/6454* (2013.01); *B01L 3/502715* (2013.01); *G01N 21/253* (2013.01); *G01N 21/6428* (2013.01); *G01N 33/54373* (2013.01); *G01N 33/54386* (2013.01); *G01N 33/582* (2013.01); *H01L 27/146* (2013.01); *B01L 7/525* (2013.01); *B01L 2300/0636* (2013.01); (Continued)

(58) Field of Classification Search
CPC ...................... G01N 21/6428; G01N 21/6486
USPC .................................. 422/82.05, 82.09, 552
See application file for complete search history.

(56) References Cited

U.S. PATENT DOCUMENTS 5,169,601 A * 12/1992 Ohta ................. G01N 33/5302
422/73
5,872,623 A    2/1999 Stabile et al.
(Continued)

FOREIGN PATENT DOCUMENTS

CN    101523198 A    9/2009
CN    104568848 A    4/2015
(Continued)

*Primary Examiner* — Natalia Levkovich
(74) *Attorney, Agent, or Firm* — IPro, PLLC; Qian Gu

(57) ABSTRACT

Disclosed herein is an apparatus comprising: a probe carrier, an optical system and a sensor; wherein the probe carrier comprises a substrate, a first layer and a second layer; wherein the substrate comprises a first surface, a second surface, one or more locations on the first surface configured to be deposit sites for one or more probes; wherein the second surface is at an opposite side of the substrate from the first surface; wherein the first layer is on the first surface of the substrate or is embedded in the substrate under the first surface; wherein the second layer is on the second surface of the substrate or is embedded in the substrate under the second surface; the first and second layers are configured to reduce crosstalk between probes at different locations.

36 Claims, 25 Drawing Sheets

(51) Int. Cl.
- G01N 21/25 (2006.01)
- H01L 27/146 (2006.01)
- G01N 33/58 (2006.01)
- B01L 3/00 (2006.01)
- G01N 33/543 (2006.01)
- G01N 21/03 (2006.01)
- B01L 7/00 (2006.01)

(52) U.S. Cl.
CPC ............... *B01L 2300/0654* (2013.01); *B01L 2300/0887* (2013.01); *G01N 21/0332* (2013.01); *G01N 2021/6471* (2013.01)

(56) References Cited

U.S. PATENT DOCUMENTS

| | | |
|---|---|---|
| 6,534,773 B1 | 3/2003 | Iwanczyk et al. |
| 2005/0221276 A1 | 10/2005 | Rozakis et al. |
| 2010/0065726 A1* | 3/2010 | Zhong .................. G01N 21/648 250/227.24 |
| 2010/0096561 A1 | 4/2010 | Johnson et al. |
| 2010/0111762 A1 | 5/2010 | Cho |
| 2010/0204064 A1 | 8/2010 | Cho |
| 2011/0174773 A1 | 7/2011 | Goshoo et al. |
| 2014/0295577 A1 | 10/2014 | Matsuzawa et al. |

FOREIGN PATENT DOCUMENTS

| | | |
|---|---|---|
| CN | 104568850 A | 4/2015 |
| JP | 2012013549 A | 1/2012 |
| JP | 2012013550 A | 1/2012 |

\* cited by examiner

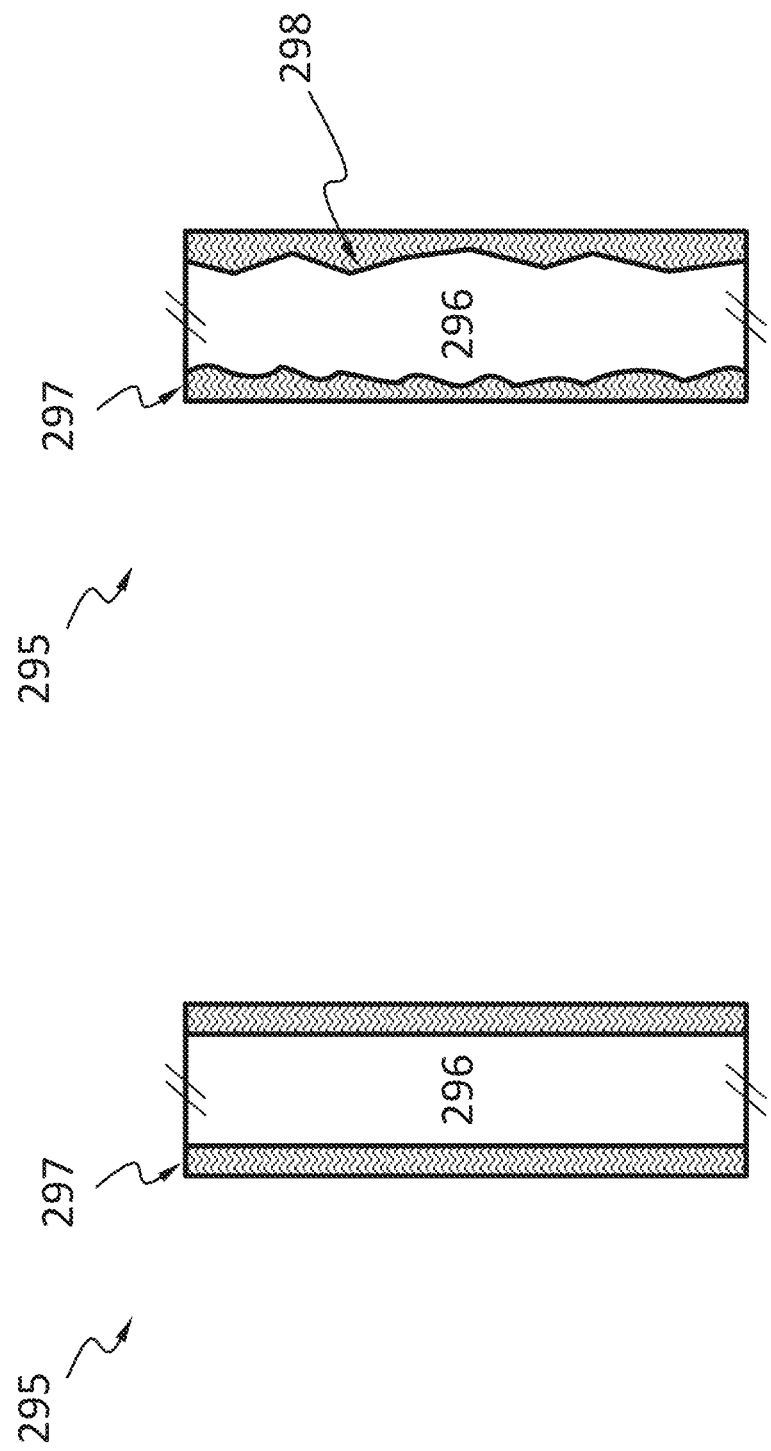

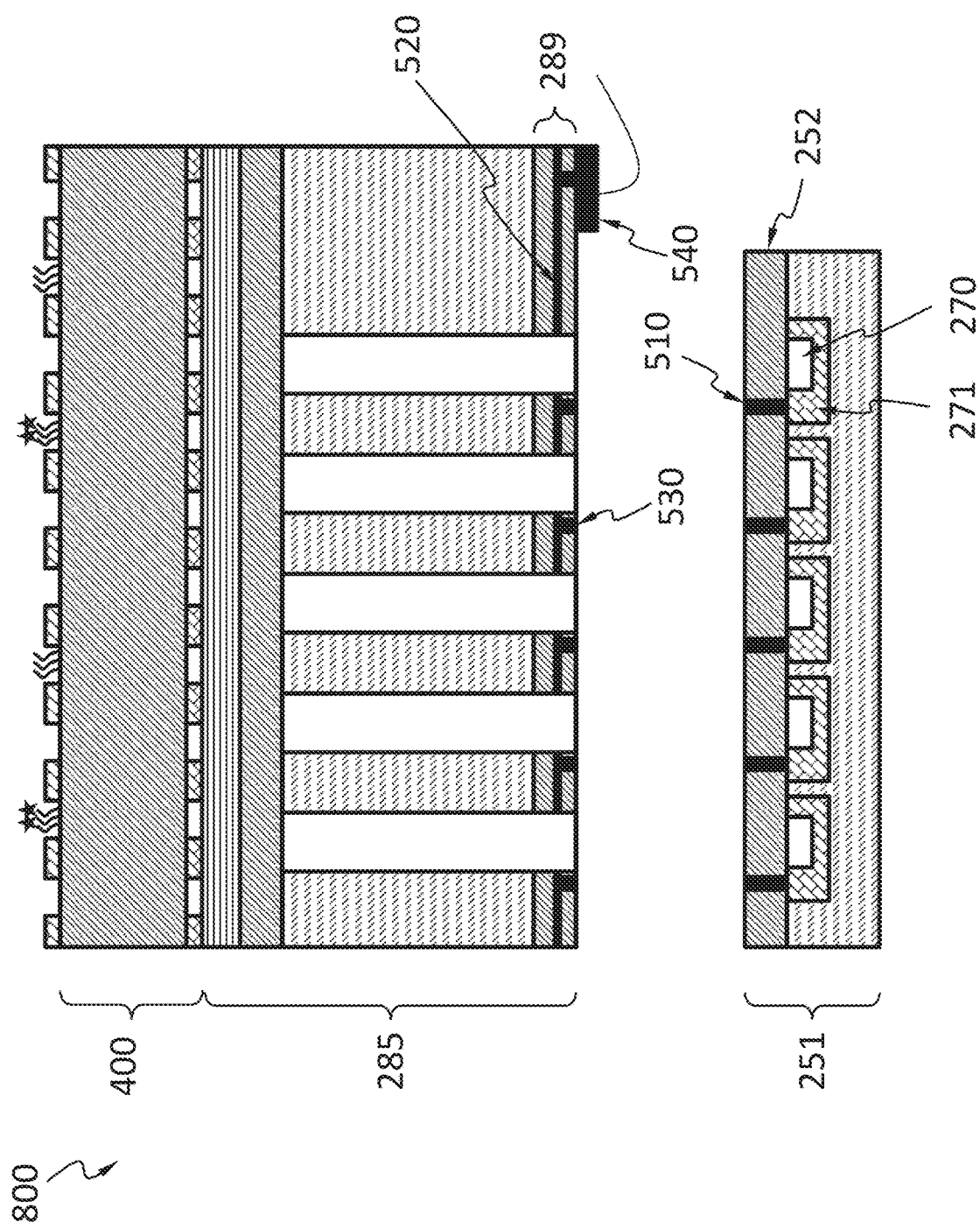

BIOSENSOR

TECHNICAL FIELD

The disclosure herein relates to biosensors, particularly biosensors based on optical detection.

BACKGROUND

A biosensor is an analytical device for detection of an analyte involved in a biological process. For example, the analyte may be a DNA, a protein, a metabolite, or even a living organism (e.g., bacteria, virus).

A biosensor usually has a probe that interacts with the analyte. The probe may be designed to bind or recognize the analyte. Examples of the probe may include antibodies, aptamers, DNAs, RNAs, antigens, etc. Interaction between the probe and the analyte may lead to one or more detectable event. For example, the detectable event may be release of a chemical species or a particle (e.g., a quantum dot), a chemical reaction, luminescence (e.g., chemiluminescence, bioluminescence, electrochemiluminescence, electroluminescence, photoluminescence, fluorescence, phosphorescence), change in a physical property (e.g., Raman scattering, color) or chemical property (e.g., reactivity, reaction rate).

A biosensor may have a detector that can detect the detectable event as a result of the interaction. The detector may transform the detectable event into another signal (e.g., image, electrical signal) that can be more easily measured and quantified. The detector may include circuitry that obtains data from the detectable event and processes the data.

One type of biosensor is microarrays. A microarray can be a two-dimensional array on a solid substrate (e.g., a glass slide, a silicon wafer). The array may have different assays at different locations. The assays at different locations may be independent controlled or measured, thereby allowing multiplexed and parallel sensing of one or many analytes. A microarray may be useful in miniaturizing diagnosis assays. For example, a microarray may be used for detecting biological samples in the fields without sophisticated equipment, or be used by a patient who is not in a clinic or hospital to monitor his or her physiological symptoms.

SUMMARY

Disclosed herein is an apparatus comprising: a probe carrier, an optical system and a sensor; wherein the probe carrier comprises a substrate, a first layer and a second layer; wherein the substrate comprises a first surface, a second surface, one or more locations on the first surface configured to be deposit sites for one or more probes; wherein the second surface is at an opposite side of the substrate from the first surface; wherein the first layer is on the first surface of the substrate or is embedded in the substrate under the first surface; wherein the second layer is on the second surface of the substrate or is embedded in the substrate under the second surface; wherein when signals are generated by the one or more probes under excitation of an excitation radiation, the first layer and the second layer are each configured to attenuate a reflective portion of the signals; wherein the first layer does not coincide with the one or more locations; wherein the second layer comprises one or more windows, each of which is aligned with one of the one or more locations to allow pass-through of the signals from the one location.

According to an embodiment, the substrate comprises silicon or glass.

According to an embodiment, the first layer comprises a roughened surface.

According to an embodiment, the first layer comprises a first absorbent material sublayer configured to absorb a transmissive portion of the signals generated from the one or more probes.

According to an embodiment, the first absorbent material sublayer comprises a broad spectrum absorbent material or a narrow band absorbent material.

According to an embodiment, the first layer comprises a first coupling material sublayer configured to reduce internal reflection of the signal in the substrate.

According to an embodiment, the first coupling material sublayer is a single-layer interference type consisting of a single quarter-wave layer of transparent material whose refractive index is about (i.e., ±20%) the square root of the substrate's refractive index.

According to an embodiment, the first coupling material sublayer is a multi-layer interference type anti-reflection coating comprising alternating layers of a low-index material and a higher-index material.

According to an embodiment, the first layer comprises a blocking material sublayer configured to block at least a portion of the excitation radiation.

According to an embodiment, the second layer comprises a second absorbent material sublayer configured to absorb a reflective portion of the signal generated from the probe.

According to an embodiment, the second absorbent material sublayer comprises a broad spectrum absorbent material or a narrow band absorbent material.

According to an embodiment, wherein the second layer comprises a second coupling material sublayer configured to reduce internal reflection of the signal in the substrate.

According to an embodiment, the second coupling material sublayer is a single-layer interference type consisting of a single quarter-wave layer of transparent material whose refractive index is about (i.e., ±20%) the square root of the substrate's refractive index.

According to an embodiment, the second coupling material sublayer is multi-layer interference type anti-reflection coating comprising alternating layers of a low refractive index material and a higher refractive index material.

According to an embodiment, the sensor comprises a plurality of pixels configured to detect the signals generated by the one or more probes under excitation of the excitation radiation.

According to an embodiment, the sensor comprises a control circuit configured to control, acquire data from, or process data from the pixels.

According to an embodiment, the pixels are optically coupled to the locations by the optical system.

According to an embodiment, the pixels are arranged in an array and are configured to be read out column by column.

According to an embodiment, the pixels are arranged in an array and are configured to be read out pixel by pixel.

According to an embodiment, the signal is luminescence

According to an embodiment, the optical system comprises a filter

According to an embodiment, the filter is configured to block at least a portion of the excitation radiation.

According to an embodiment, the filter is a dichroic filter.

According to an embodiment, the filter comprises a metamaterial, quantum dots or a photonic crystal.

According to an embodiment, the optical system comprises transmissive layer

According to an embodiment, the optical system comprises a plurality of microlens.

According to an embodiment, the optical system comprises a plurality of collimators.

According to an embodiment, the collimators comprise a meta-material, quantum dots or a photonic crystal.

According to an embodiment, the collimators are configured to eliminate optical cross-talk between neighboring pixels among the plurality of pixels.

According to an embodiment, at least one of the collimators comprises a core and a sidewall surrounding the core.

According to an embodiment, the core is a material that essentially prevents the excitation radiation from passing through irrespective of propagation direction of the excitation radiation.

According to an embodiment, the core comprises a dichroic filter.

According to an embodiment, the core allows the signal to pass through essentially unabsorbed.

According to an embodiment, the core is a void space.

According to an embodiment, the sidewall attenuates a portion of the signal reaching the sidewall.

According to an embodiment, the sidewall is textured.

BRIEF DESCRIPTION OF FIGURES

FIG. 3C schematically shows a collimator, according to an embodiment.

FIG. 3D schematically shows a collimator, according to an embodiment.

DETAILED DESCRIPTION

Figure 1A:
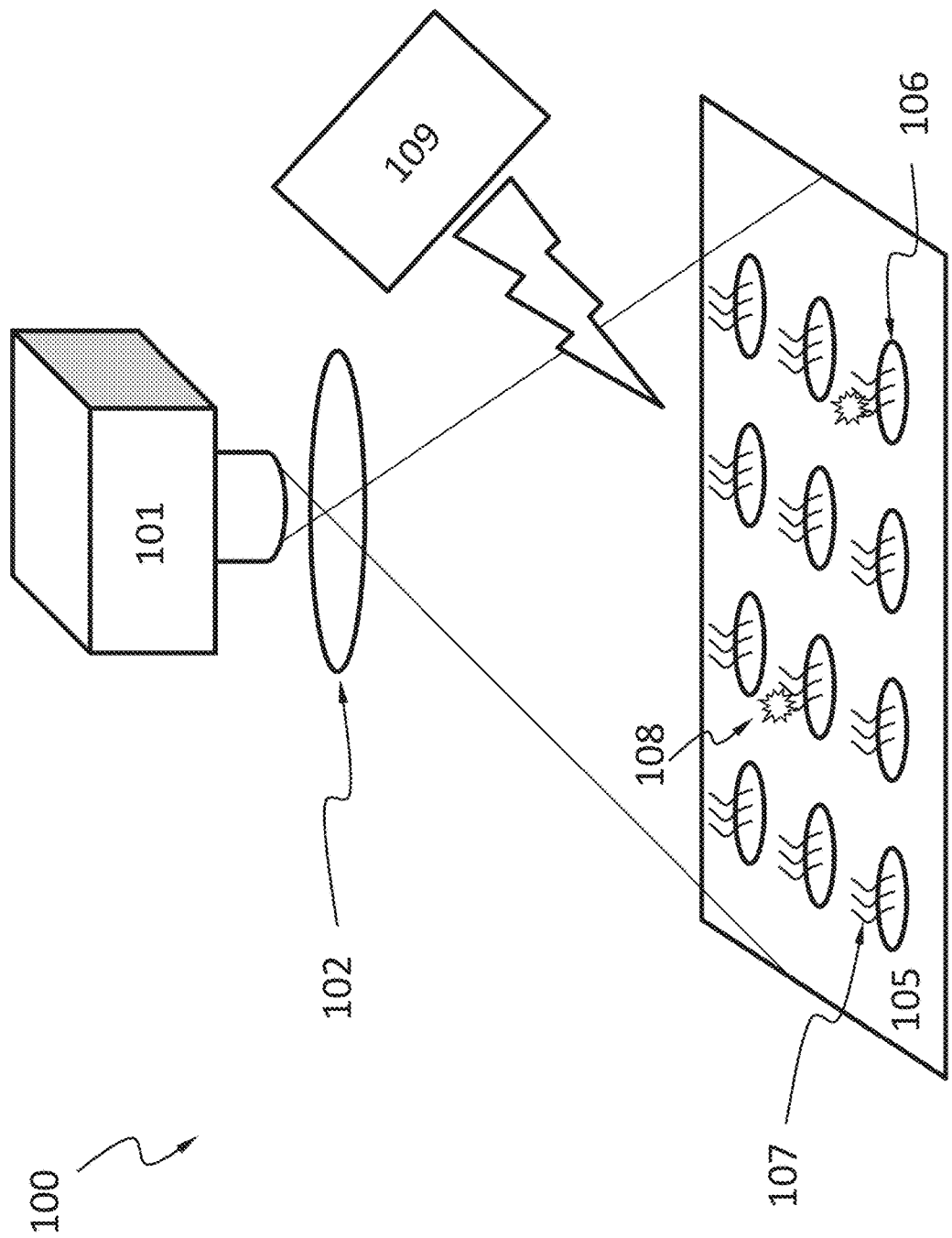
FIG. 1A schematically shows an apparatus including a microarray.

FIG. 1A schematically shows an apparatus 100 including a microarray 105. The system 100 may have an image sensor 101, an optical system 102, and/or an excitation source 109. The image sensor 101 may be configured to measure an optical property (e.g., color, intensity) at different locations 106 of the microarray 105. The locations 106 may have various probes 107 attached thereto. The probes 107 may interact with analyte and the interaction may generate signals 108 detectable by the image sensor 101. The generation of the signals 108 may need excitation by the excitation source 109 (e.g., laser, UV light, etc.). The image sensor 101 and the optical system 102 of the apparatus 100 tend to be bulky, fragile, or expensive and may not have high enough spatial resolution to distinguish one location from its neighboring locations.

Figure 1B:
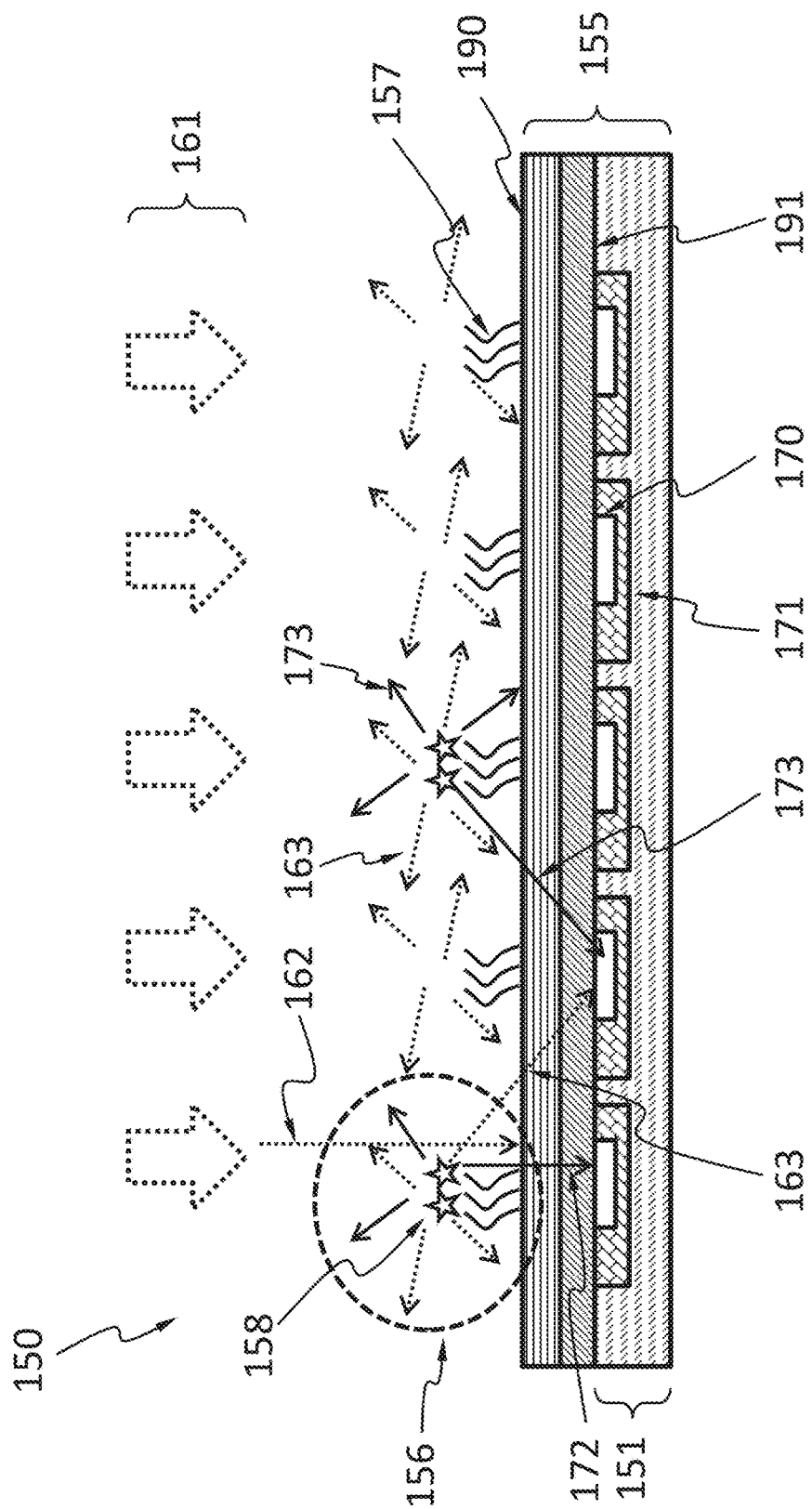
FIG. 1B schematically shows an apparatus where detector capability is integrated into a microarray.

FIG. 1B schematically shows an apparatus 150 where detector capability is integrated into a microarray 155. The microarray 155 may have multiple locations 156 with various probes 157 attached thereto. The probes 157 may interact with various analytes and the interaction may generate signals 158 detectable by a sensor 151 integrated to the microarray 155. For example, the analytes are fluorophore-labeled nucleic acid or protein fragments; the probes are oligonucleotides or antibodies. Locations with fluorophore-labeled analytes captured by the probes can be identified by detecting fluorescence from the fluorophores on the captured analytes. The sensor 151 may have multiple pixels 170 configured to detect the signals 158 (e.g., color, intensity). The pixels 170 may have a control circuit 171 configured to control, acquire data from, and/or process data from the pixels 170. The pixels 170 may be arranged such that each pixel 170 is optically coupled to one of the locations 156. However, the signals 158 generated at one location 156 may not entirely reach the pixel 170 optically coupled to that location 156. A portion 172 of the signals 158 may reach the pixel 170 optically coupled to that location 156 but another portion 173 may be scattered into neighboring pixels ("optical cross-talk") and/or away from all pixels 170. Generating the signals 158 may need an excitation radiation 161 (e.g., laser, UV light, etc.). A portion 162 of the excitation radiation 161 may pass through the locations 156 unscattered. A portion 163 of the excitation radiation 161 may be scattered into some of the pixels 170 or away from all pixels 170. The portion 162 may be blocked by a filter 190 from reaching the pixels 170. The filter 190 may be positioned below or above a transmissive layer 191. However, the filter 190 may be sensitive to incident directions and may not block the portion 163, despite portions 162 and 163 have the same wavelength. If the portion 163 reaches the pixels 170, it can overshadow signals 158.

Figure 2A:
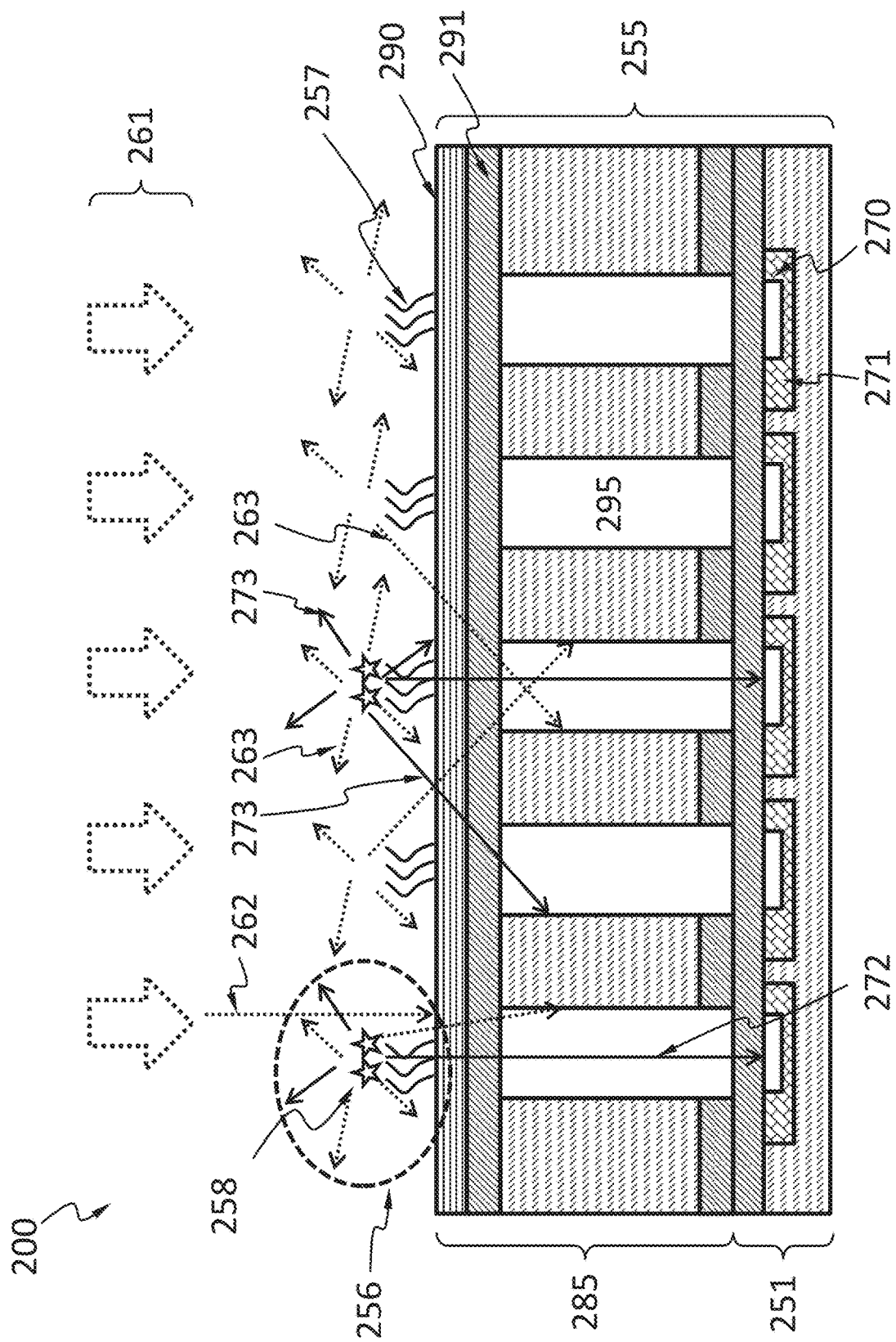
FIG. 2A schematically shows an apparatus, according to an embodiment.
Figure 2B:
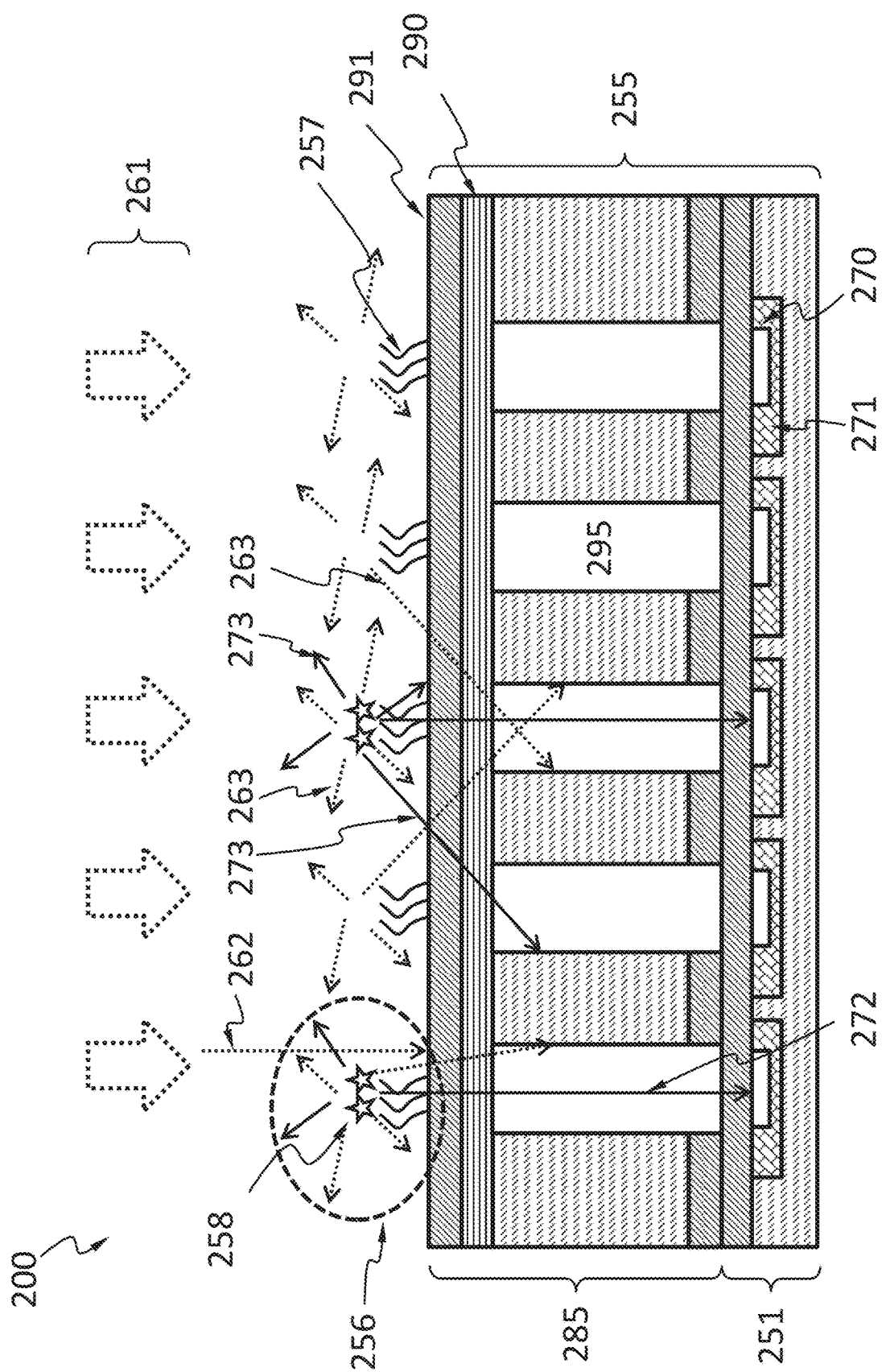
FIG. 2B schematically shows an apparatus, according to an embodiment.

FIG. 2A schematically shows an apparatus 200. The system 200 includes a microarray 255 including an integrated sensor 251 and an optical system 285. The microarray 255 may have multiple locations 256 with various probes 257 attached thereto. The probes 257 may interact with various analytes and the interaction may generate signals 258 detectable by the sensor 251. The sensor 251 may have multiple pixels 270 configured to detect the signals 258 (e.g., color, intensity). The pixels 270 may have a control circuit 271 configured to control, acquire data from, and/or process data from the pixels 270. The pixels 270 may be arranged such that each pixel 270 is optically coupled to one or more of the locations 256. The optical system 285 may include a filter 290 positioned below or above a transmissive layer 291 (FIG. 2B shows an example where the filter 290 is below the transmissive layer 291). The optical system 285 may include a plurality of collimators 295 configured to optically couple the pixels 270 to the locations 256. The filter 290 and the transmissive layer 291 may not have to be fabricated on the same substrate as the collimators 295. Instead, the filter 290 and the transmissive layer 291 may be fabricated and bonded to the collimators 295. The sensor 251 may comprise quantum dots.

The transmissive layer 291 may include oxide or nitride. For example, the transmissive layer 291 may include glass.

The filter 290 may be a dichroic filter (also known as interference filter). The filter 290 may be a low-pass (passing frequency below a threshold) or band-pass filter. The filter 290 may include a meta-material, quantum dots or a photonic crystal. A meta-material has component materials arranged in repeating patterns, often at microscopic or smaller scales that are smaller than the wavelengths of the light the meta-material is designed to influence. The structure of the repeated patterns and the properties of the component materials may be selected to tailor the properties of the meta-material. For example, the meta-material may provide optical transparency at all frequencies except at the selected frequency or frequencies which it is configured to block (for example particular laser frequencies that could cause harm to a user). A photonic crystal is a periodic dielectric structure that has a band gap that forbids propagation of a certain frequency range of light. The filter 290 may have multiple thin layers of materials with different refractive indices and may be made by alternately depositing thin layers of these materials. A quantum dot (QD) is a nanocrystal made of semiconductor materials that is small enough to exhibit quantum mechanical properties. Specifically, its excitons are confined in all three spatial dimensions. Quantum dots of the same material, but with different sizes, can absorb light of different wavelengths due to the quantum confinement effect. The larger the quantum dot, the redder (lower energy) its absorption. Conversely, smaller quantum dots absorb bluer (higher energy) light. The filter 290 may be an absorptive filter but it would have sufficient thickness to be effective.

In an embodiment, the filter 290, the transmissive layer 291 if present, and the collimator 295 may be integrated on the same substrate.

In an embodiment, the transmissive layer 291 may be an insulating material such as silicon oxide or silicon nitride. In an embodiment, the transmissive layer 291 may even be omitted.

In an embodiment, the collimator 295 may be configured to essentially prevent (e.g., prevent more than 90%, 99%, or 99.9% of) light from passing if the deviation of the propagation direction of the light from an optical axis of the collimator 295 is greater than a threshold (e.g., 20°, 10°, 5°, or 1°). A portion 272 of the signals 258 may propagate towards the pixel 270 optically coupled to that location 156 but another portion 273 may be scattered towards neighboring pixels ("optical cross-talk") and/or away from all pixels 270. The collimator 295 may be configured to essentially eliminate optical cross-talk by essentially preventing the portion 273 from passing through the collimator 295. Generating the signals 258 may need an excitation radiation 261 (e.g., laser, UV light, etc.). A portion 262 of the excitation radiation 261 may pass through the locations 256 unscattered. A portion 263 of the excitation radiation 261 may be scattered into other directions towards some of the pixels 270 or away from all pixels 270. The portion 262 may be blocked by the filter 290 from reaching the pixels 270. The filter 290 may be sensitive to incident directions and may not block the portion 263, despite portions 262 and 263 have the same wavelength. The collimators 295 may be configured to essentially prevent the excitation radiation from passing through irrespective of the propagation direction, or to essentially prevent the portion 263 scattered away from the propagation direction of the portion 261 from passing through.

In an embodiment, each of the collimators 295 extends from one of the locations 256 to the pixel 270 optically coupled to that one location.

In an embodiment, the collimator 295 may have a core 296 surrounded by a sidewall 297.

Figure 3B:
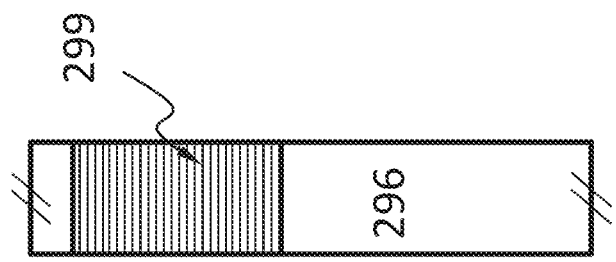
FIG. 3B schematically shows a collimator, according to an embodiment.
Figure 3A:
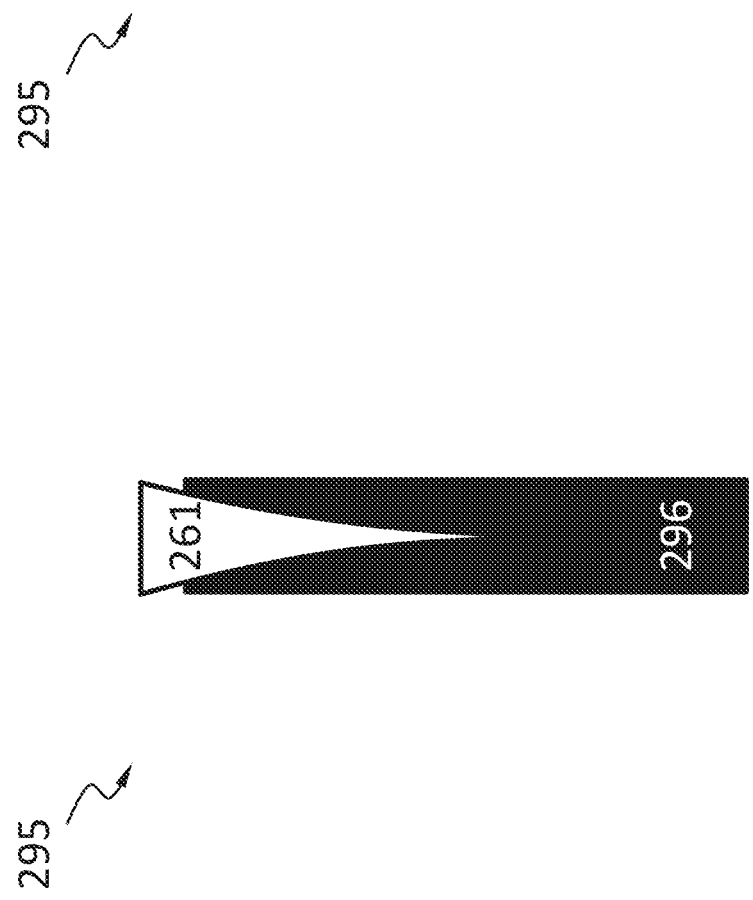
FIG. 3A schematically shows a collimator, according to an embodiment.

In an embodiment schematically shown in FIG. 3A, the core 296 may be a material that essentially prevents (e.g., prevents more than 90%, 99%, or 99.9% of) the excitation radiation 261 from passing through irrespective of the propagation direction of the excitation radiation 261. For example, the core 296 may be a material that attenuates (absorbs) the excitation radiation 261. The core 296 may allow the signals 258 to pass through essentially unabsorbed. In this embodiment, the filter 290 may be omitted.

In an embodiment schematically shown in FIG. 3B, the core 296 may have a structure 299 that essentially prevents (e.g., prevents more than 90%, 99%, or 99.9% of) a portion of the excitation radiation 261 from passing through if the deviation of the propagation direction of the portion (e.g., portion 272) from the optical axis of the collimator 295 is smaller than a threshold (e.g., 20°, 10°5°, or 1°). For example, the structure 299 may have a dichroic filter, a meta-material, quantum dots or a photonic crystal. The core 296 may allow the signals 258 to pass through essentially unabsorbed (i.e., less than 10% absorbed). In this embodiment, the filter 290 may be omitted.

In an embodiment, schematically shown in FIG. 3C, the sidewall 297 of the collimator 295 may attenuate (absorb) the excitation radiation. The portion 263 of the excitation radiation 261 may pass through the filter 290 and enter the collimator 295 but is likely to reach the sidewall 297 before it can reach the pixels 270. The sidewall 297 that can attenuate (absorb) the excitation radiation will essentially prevent stray excitation radiation from reaching the pixels 270. In an embodiment, the core 296 may be a void space. Namely, the sidewall 297 surrounds a void space.

In an embodiment, the sidewall 297 may attenuate (absorb) any portion of the signal 258 reaching the sidewall, which will essentially prevent optical cross-talk.

In an embodiment, schematically shown in FIG. 3D, the sidewall 297 is textured. For example, the interface 298 between the sidewall 297 and the core 296 (which can be a void space) may be textured. Textured sidewall 297 can help further attenuate light incident thereon.

In an embodiment, the filter 290 and the transmissive layer 291 may be both omitted. The collimator 295 may have a top surface 294 exposed. The top surface 294 may be of a different material from its neighboring surface, thereby facilitating functionalization of the top surface 294. The probes 457 may be selectively attached directly to the top surface 294.

Figure 3F:
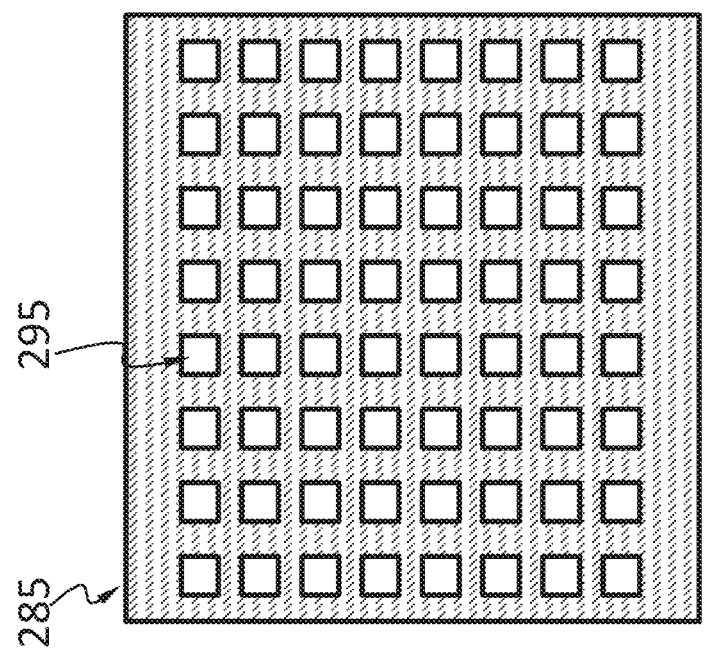
FIG. 3E and FIG. 3F schematically show that the optical system may have a plurality of collimators arranged in an array.
Figure 3E:
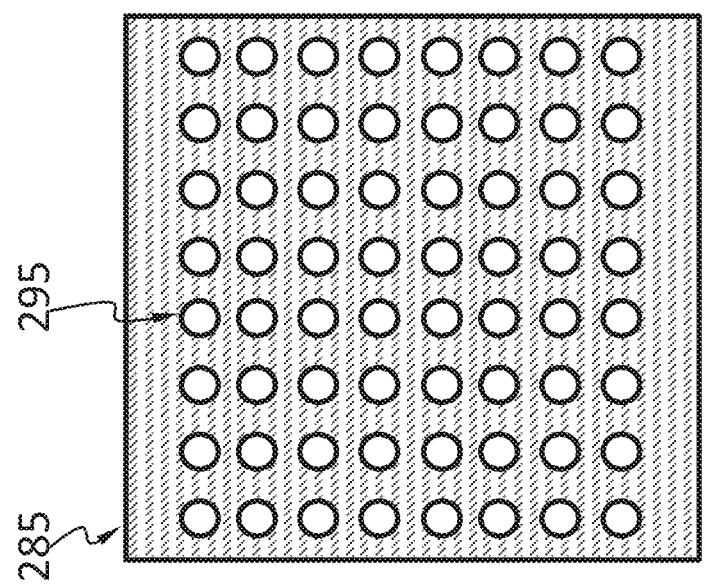

In an embodiment, schematically shown in FIG. 3E and FIG. 3F, the optical system 285 may have a plurality of collimators 295 arranged in an array. For example, the optical system 285 may have a dedicated collimator 295 for each pixel 270. For example, the optical system 285 may have a collimator 295 shared by a group of pixels 270. The collimator 295 may have any suitable cross-sectional shape, such as circular, rectangular, and polygonal.

In an embodiment, the collimators 295 may be made by etching (by e.g., deep reactive ion etching (deep RIE), laser drilling) holes into a substrate. The sidewall 297 may be made by depositing a material on the sidewall of the holes. The core 296 may be made by filling the holes. Planarization may also be used in the fabrication of the collimators 295.

In an embodiment, the filter 290 may be omitted or its function may be integrated into the collimators 295.

Figure 4A:
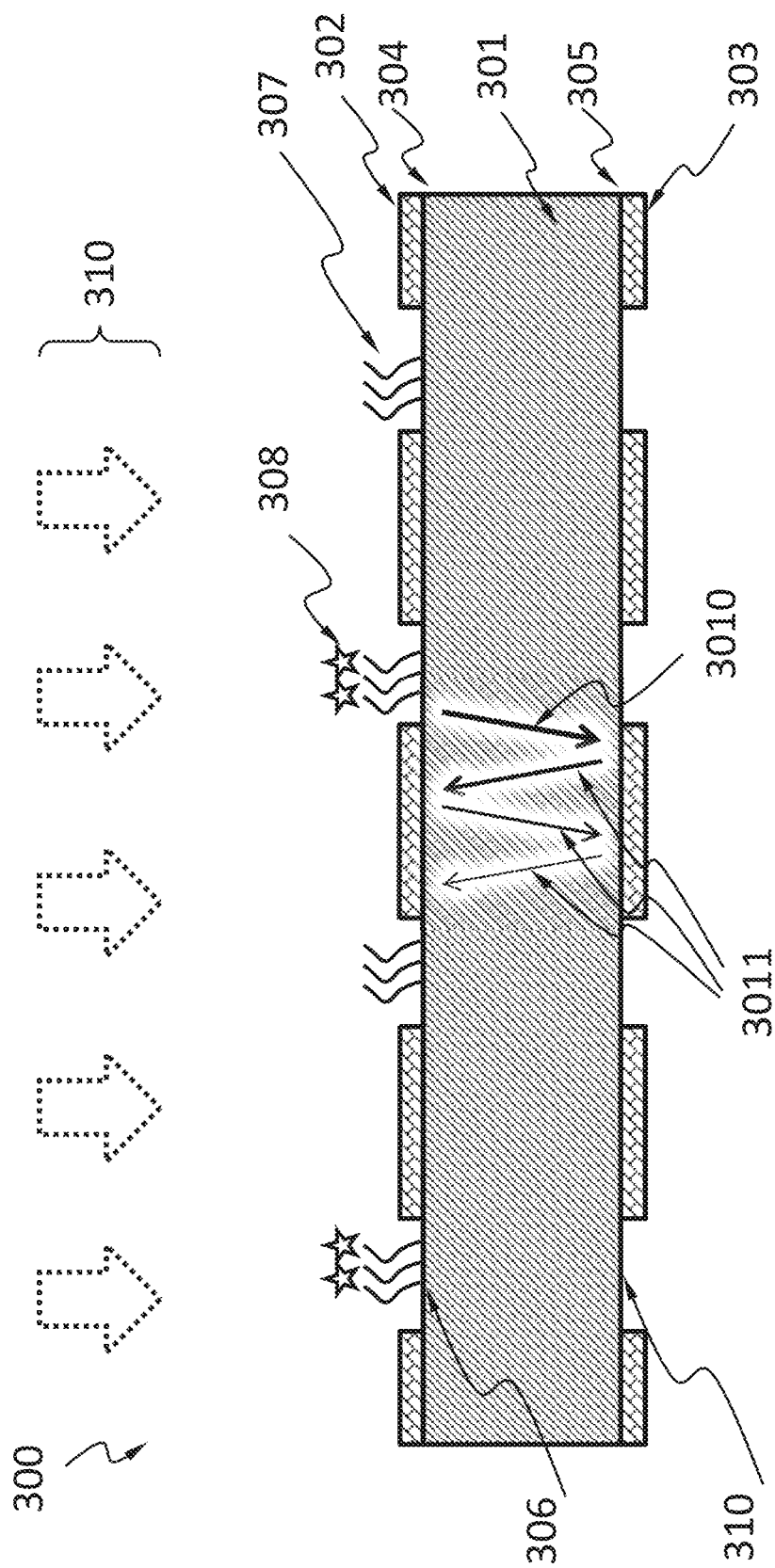
FIG. 4A schematically shows a probe carrier 300, according to an embodiment.

FIG. 4A schematically shows a probe carrier 300, according to an embodiment. The probe carrier comprises a substrate 301, a first layer 302 and a second layer 303. The substrate comprises a first surface 304, a second surface 305, and one or more locations 306 on the first surface configured to be deposit sites for one or more probes 307. The second surface 305 is at an opposite side of the substrate 301 from the first surface 304.

Figure 4B:
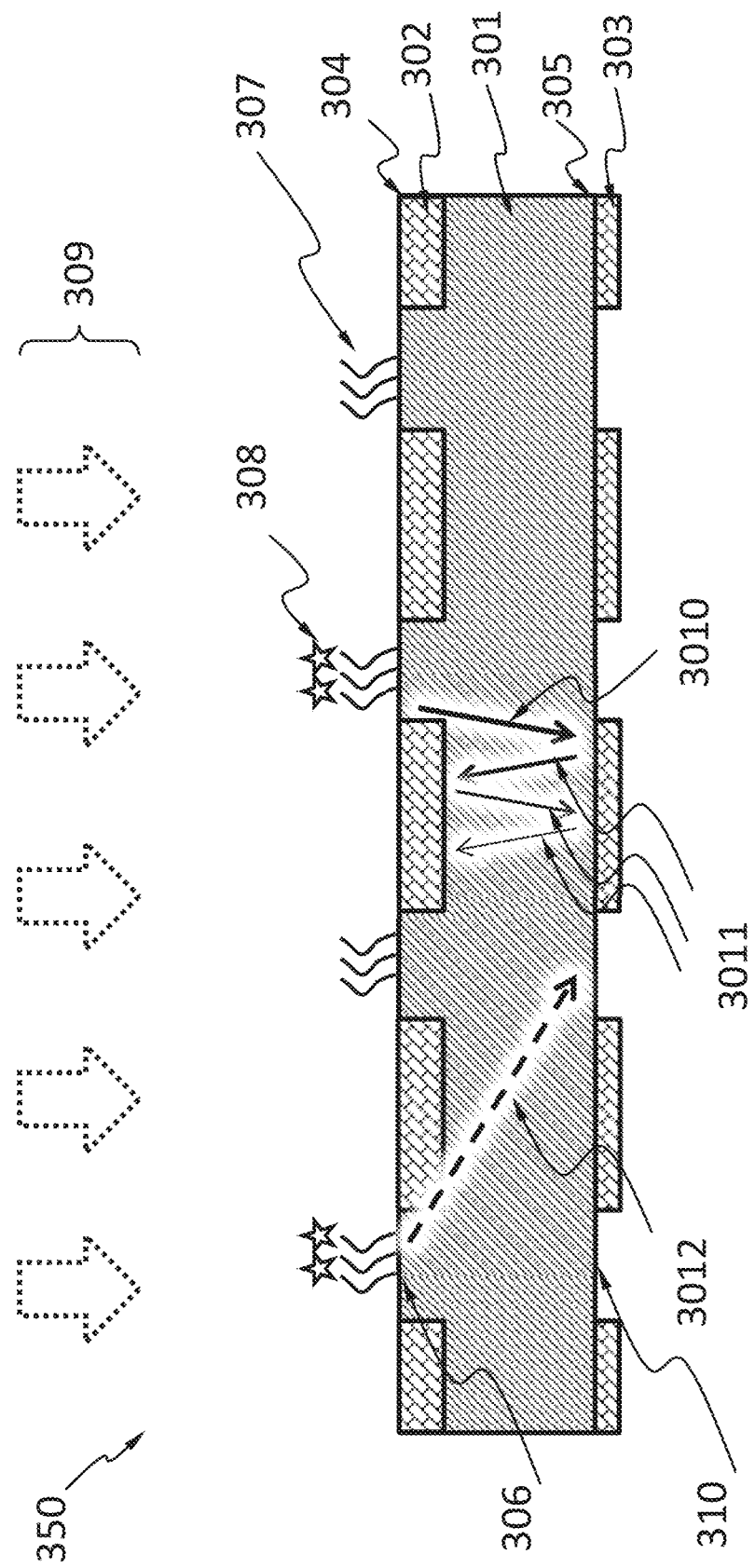
FIG. 4B schematically shows a probe carrier 350, according to an embodiment.

In an embodiment as shown in FIG. 4A, the first layer 302 is on the first surface 304 of the substrate 301. Alternatively, in an embodiment as shown in FIG. 4B, in probe carrier 350, the first layer 302 may be embedded in the substrate 301 under the first surface 304. The first layer 302 may be partially on and partially embedded in the first surface 304.

In the embodiment as shown in FIG. 4A, the second layer 303 is on the second surface 305 of the substrate 301. In an embodiment, the second layer 303 may be embedded in the substrate 301 under the second surface 305.

That a layer is on a surface, in this context, does not exclude that the layer can be partially embedded in the surface. That a layer is embedded in a surface, in this context, does not exclude that the layer can be partially on the surface.

As shown in FIG. 4A or 4B, after probes 307 are attached to the probe carrier 301, signals 308 (e.g., light) may be generated by the one or more probes 307 under excitation of an excitation radiation 309. A transmissive portion 3010 of the signal 308 enters the substrate 301 of the probe carrier 301.

According to an embodiment, the substrate may comprise silicon or glass. The substrate may also comprise other material suitable for the transmission of the signal from the probes 307.

In general, when a wave (e.g., light wave) is incident on the surface of an object, it may be absorbed, reflected or transmitted. When the transmissive portion 3010 travels to the second surface, a fraction of 3010 is transmitted to the exterior of substrate and may be received by a sensor. In addition, another fraction of 3010 may be absorbed at the second surface 305, in which case its energy is converted to heat; and still another fraction of 3010, that is a reflective portion 3011, may be reflected at the second surface 305 and continues to travel within the substrate 301. Similarly, reflective portions 3011 of the signals 308 may generate other reflections at the boundary surface of the substrate 301 due to internal reflections at the first surface 304 and second surface 305. Both the transmissive portion 3010 and the reflective portion 3011 of the signals 308 may be collected by an optical system or a sensor, if both reach and transmit through the second surface 305. Although the reflective portions 3011 is only a fraction of the signals and are relatively reduced in intensity at each internal reflection, some reflective portions 3011 may still worsen the spatial resolution of the apparatus if it is received by the sensor of the apparatus.

According to embodiment as shown in FIG. 4A or 4B, the first layer 302 and the second layer 303 are each configured to attenuate the reflective portion 3011 of the signals 308. As a reflective portion 3011 travels further in the substrate 301, signals from different probe locations are more prone to be mixed up and spatial resolution at the downstream sensor becomes more difficult. Attenuation of the reflective portion 3011 may reduce or eliminate signal mix up from different probe locations, and therefore increase spatial resolution of the biosensor apparatus.

As used herein, attenuation of a reflective portion of a signal refers to both increased absorption of a fraction of incident signal at a surface and decreased reflection of a fraction of incident signal at a surface, relative to an otherwise identical device without layers 302 and 303.

As used herein, spatial resolution refers to the differentiation of signals from different probe locations by the apparatus.

As used herein, a transmissive portion of the signal refers to the portion of the signal that transmits directly through the substrate from the surface where the signal originates to the opposite surface.

As used herein, a reflective portion of the signal refers to the portion of the signal that has undergone internal reflection in the substrate.

According to embodiment as shown in FIG. 4A or 4B, the first layer 302 does not coincide with the one or more locations 306 for probes. That is, the first layer 302 and the one or more locations 306 for probes do not overlap.

According to embodiment as shown in FIG. 4A or 4B, the second layer 303 comprises one or more windows 310. The one or more locations 306 are in the windows 310.

In the embodiment as shown in FIG. 4B, the depth of the embedded portion of the first layer 302 may block a transmissive portion 3012 of the signals 308 which is directed to a window 10 that is not aligned to the probe that generates such transmissive portion 3012 of the signals 308.

Figure 5A:
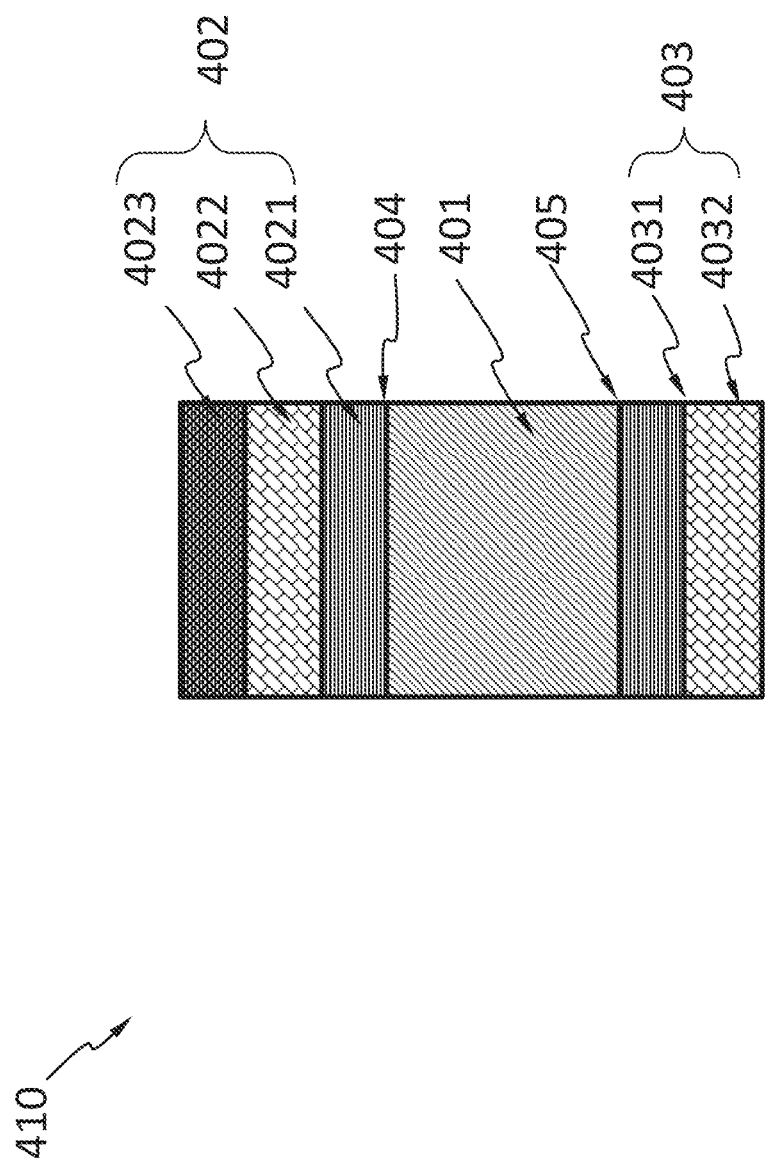
FIG. 5A schematically shows a cross sectional view of a probe carrier 400, according to an embodiment.
Figure 5B:
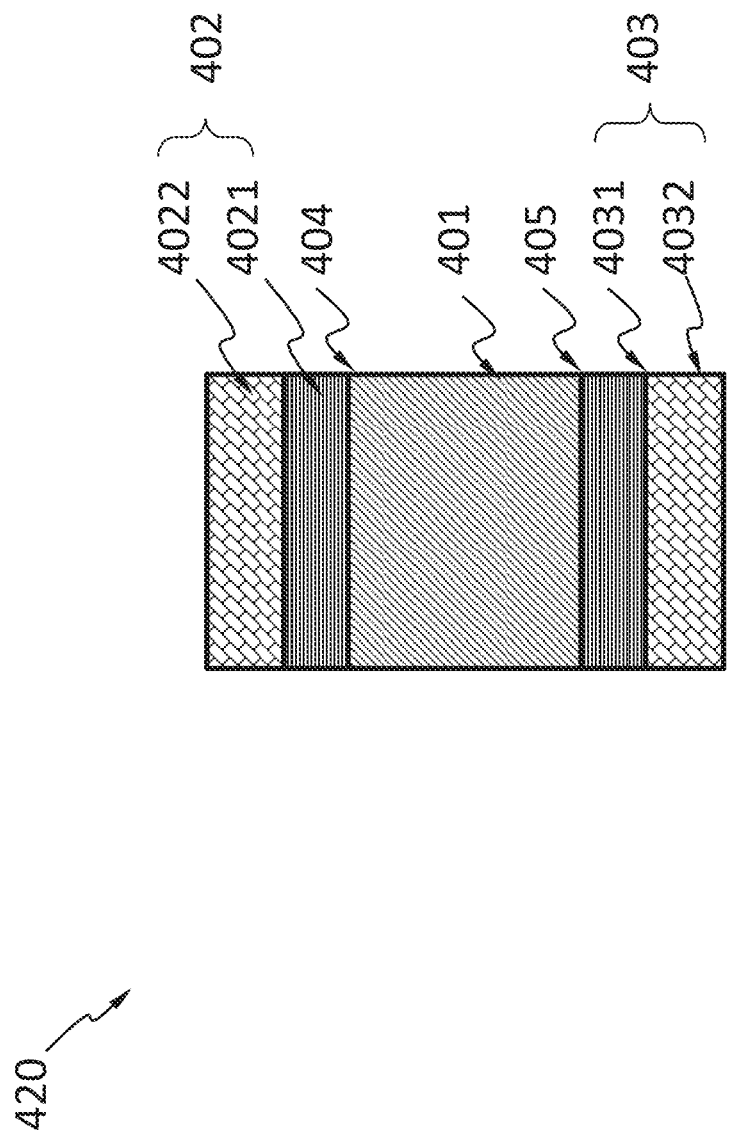
FIG. 5B schematically shows a cross sectional view of a probe carrier 410, according to an embodiment.
Figure 5C:
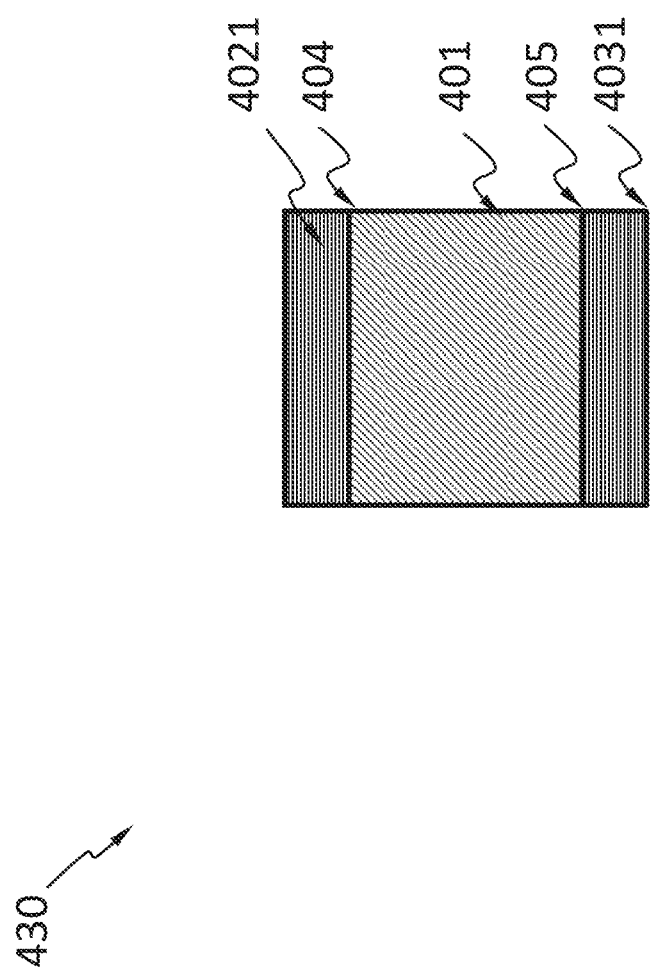
FIG. 5C schematically shows a cross sectional view of a probe carrier 420, according to an embodiment.

FIG. 5A, 5B or 5C each schematically show a partial cross sectional view of probe carriers 410, 420 and 430, respectively. As shown in FIG. 5A, a substrate 401 comprises a first layer 402, a second layer 403, a first surface 404 and a second surface 405. The first layer 402 comprises a first coupling material sublayer 4021 configured to reduce internal reflection of the signal in the substrate, a first absorbent material sublayer 4022 configured to absorb a transmissive portion of the signals generated from the one or more probes, and a blocking material sublayer 4023 configured to block at least a portion of the excitation radiation. As shown in FIG. 5A, the second layer 403 comprises a second absorbent material sublayer 4032 configured to absorb a reflective portion of the signal generated from the probe, and a second coupling material sublayer 4031 configured to reduce internal reflection of the signal in the substrate.

In an embodiment, the first coupling material sublayer 4021 is a single-layer anti-reflection coating with a thickness of $\lambda_0/(4n_1)$, where $\lambda_0$ is the vacuum wavelength of the signal and $n_1$ is the refractive index of the material of the layer 4021.

In an embodiment, the first coupling material sublayer 4021 is a multi-layer interference type anti-reflection coating comprising alternating layers of a low-index material and a high-index material. In an embodiment, the first coupling material sublayer 4021 is an absorbing anti-reflection coating.

In an embodiment, the first absorbent material sublayer 4022 may comprise a roughened surface. In an embodiment, the first absorbent material sublayer 4022 comprises a broad spectrum absorbent material. As used herein, a broad spectrum absorbent material absorbs both signals from the probes and at least another signal at a different wavelength from the signals form the probes. In an embodiment, the first absorbent material sublayer 4022 comprises a narrow band absorbent material. As used herein, a narrow band absorbent material absorbs signals essentially only at the wavelength of the signals from the probes.

Some other embodiments of arrangements of the first layer and second layers are shown in FIGS. 5B and 5C. As shown in FIG. 5B, the probe carrier 420 has a first layer 402, a second layer 403, a first surface 404 and a second surface 405 and does not comprise a blocking material sublayer in the first layer 402, in contrast with the probe carrier 410 in FIG. 5A. As shown in FIG. 5C, blocking material sublayer 4023 and both the first absorbent material sublayer 4022 and the second absorbent material sublayer 4032 are omitted in the probe carrier 430, in contrast with the probe carrier 410 in FIG. 5A.

Arrangement of the biosensor apparatus with microarrays, optical system and sensors are further illustrated below.

Figure 6:
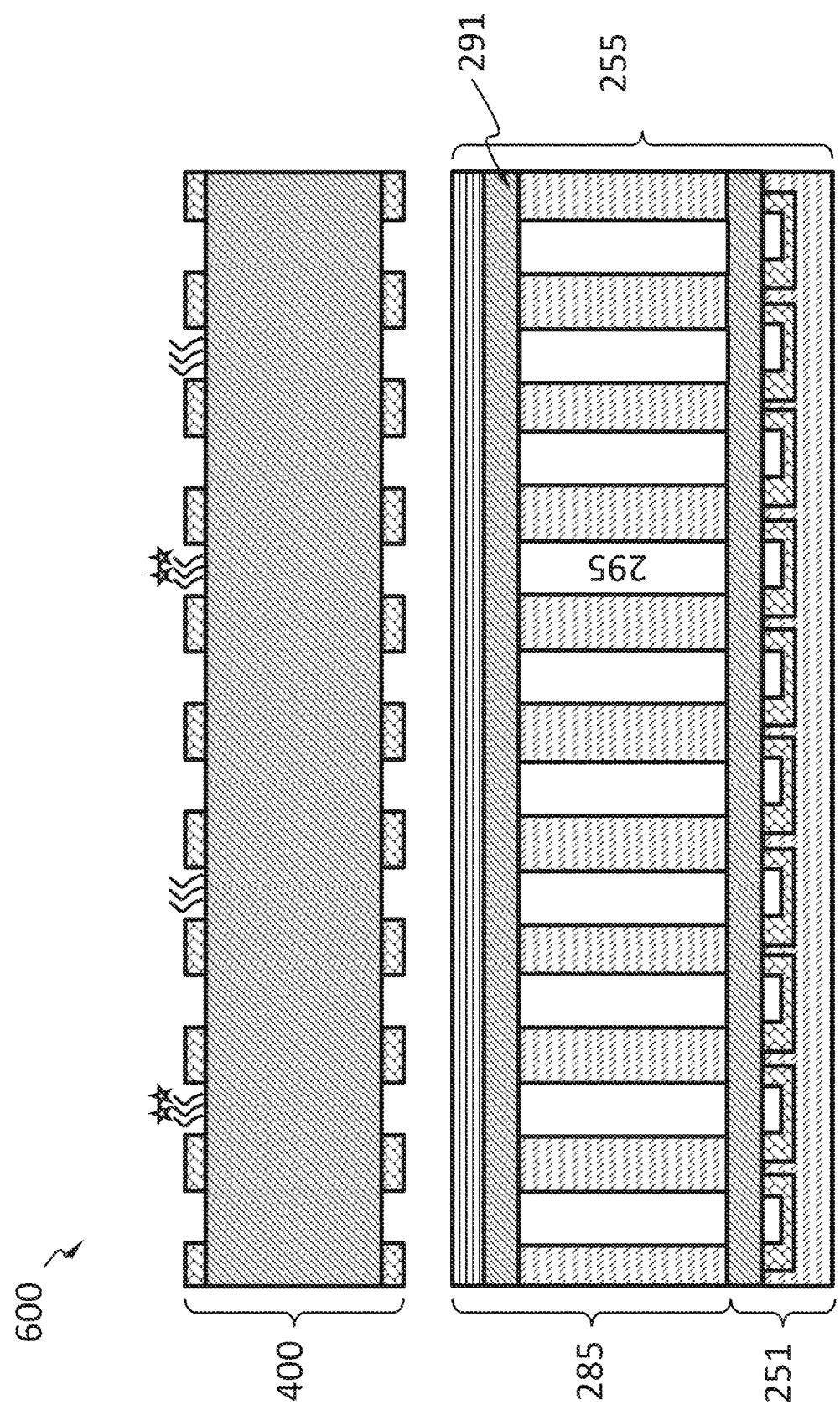
FIG. 6 schematically shows an apparatus with an optical system, according to an embodiment.

In an embodiment as shown in FIG. 6, an apparatus 600 comprises a probe carrier 400 and a microarray 255 that comprises an optical system 285 with collimators 295 and an integrated sensor 251. The probe carrier 400 may be mounted to the microarray 255 with a suitable technique. The biosensor function of the apparatus 500 may be carried out with appropriate probes on the probe carrier 400. In other embodiments other examples of probe carriers including but not limited to the probe carrier 410 or 420 may be used.

In an embodiment as schematically shown in FIG. 6, in apparatus 600, the optical system 285 may have a microfluidic system 850 to deliver reactants such as the analyte and reaction product to and from the locations 256. The microfluidic system 850 may have wells, reservoirs, channels, valves or other components. The microfluidic system 850 may also have heaters, coolers (e.g., Peltier devices), or temperature sensors. The heaters, coolers or temperature sensors may be located in the optical system 285, above or in the collimators 295. The heaters, coolers or temperature sensors may be located above or in the sensor 251. The biosensor apparatus 800 may be used for a variety of assays. For example, the biosensor apparatus 800 can be used to conduct real-time polymerase chain reaction (e.g., quantitative real-time PCR (qPCR)). Real-time polymerase chain reaction (real-time PCR) detects amplified DNA as the reaction progresses. This is in contrast to traditional PCR where the product of the reaction is detected at the end. One real-time PCR technique uses sequence-specific probes labelled with a fluorophore which fluoresces only after hybridization of the probe with its complementary sequence, which can be used to quantify messenger RNA (mRNA) and non-coding RNA in cells or tissues. In other embodiments other examples of probe carriers including but not limited to the probe carrier 410 or 420 may be used.

The optical system 285 and the sensor 251 may be fabricated in separate substrates and bonded together using a suitable technique, such as, flip-chip bonding, wafer-to-wafer direct bonding, or gluing.

Figure 7:
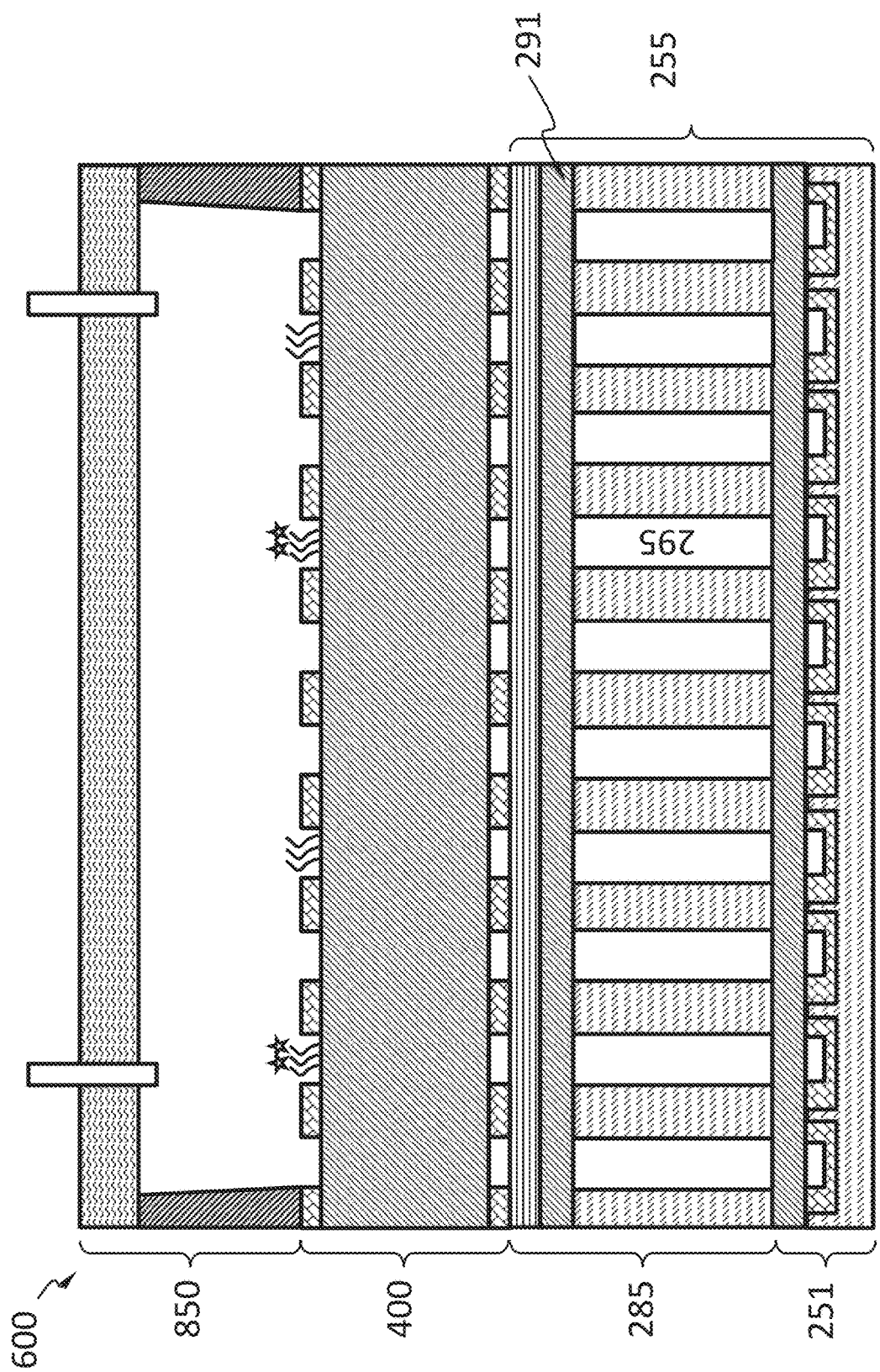
FIG. 7 schematically shows an apparatus in which the optical system may have a microfluidic system, according to an embodiment FIG. 8A schematically shows an apparatus wherein a sensor ay may have a signal transfer layer and that the optical system in the microarray may have a redistribution layer, according to an embodiment.

In the embodiment as shown in FIG. 6 or FIG. 7, each location is aligned with one of the collimators. This is achieved by controlled fabrication process such that the location in the probe carrier has a same width as the width of the collimators in the microarray, and appropriate alignment of the probe carrier with the microarray is required during assembly of the probe carrier with the microarray to form the biosensor apparatus.

In other embodiments, other types of microarrays may be used with any of the aforementioned probe carriers to form a biosensor apparatus. Some examples of such microarrays are illustrated as below.

In an embodiment, schematically shown in FIG. 8A, in apparatus 800, the sensor 251 has a signal transfer layer 252. The signal transfer layer 252 may have a plurality of vias 510. The signal transfer layer 252 may have electrically insulation materials (e.g., silicon oxide) around the vias 510. The optical system 285 may have a redistribution layer 289 with transmission lines 520 and vias 530. The transmission lines 520 connect the vias 530 to bonding pads 540. When the sensor 251 and the optical system 285 are bonded, the vias 510 and the vias 530 are electrically connected. This configuration shown in FIG. 8A allows the bonding pads 540 to be positioned away from the probes 257.

Figure 8B:
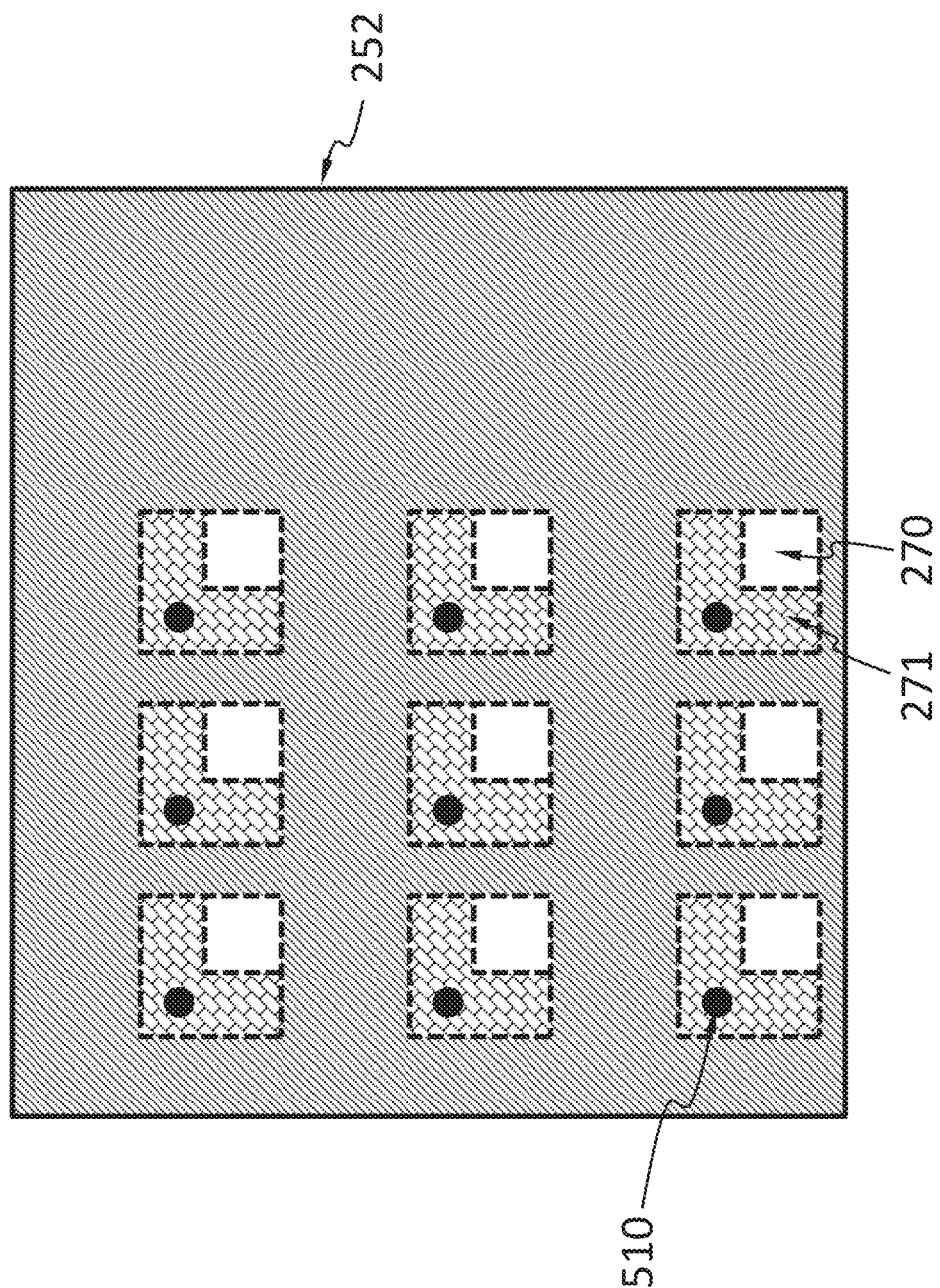
FIG. 8B schematically shows a top view of the sensor in FIG. 8A.
Figure 8C:
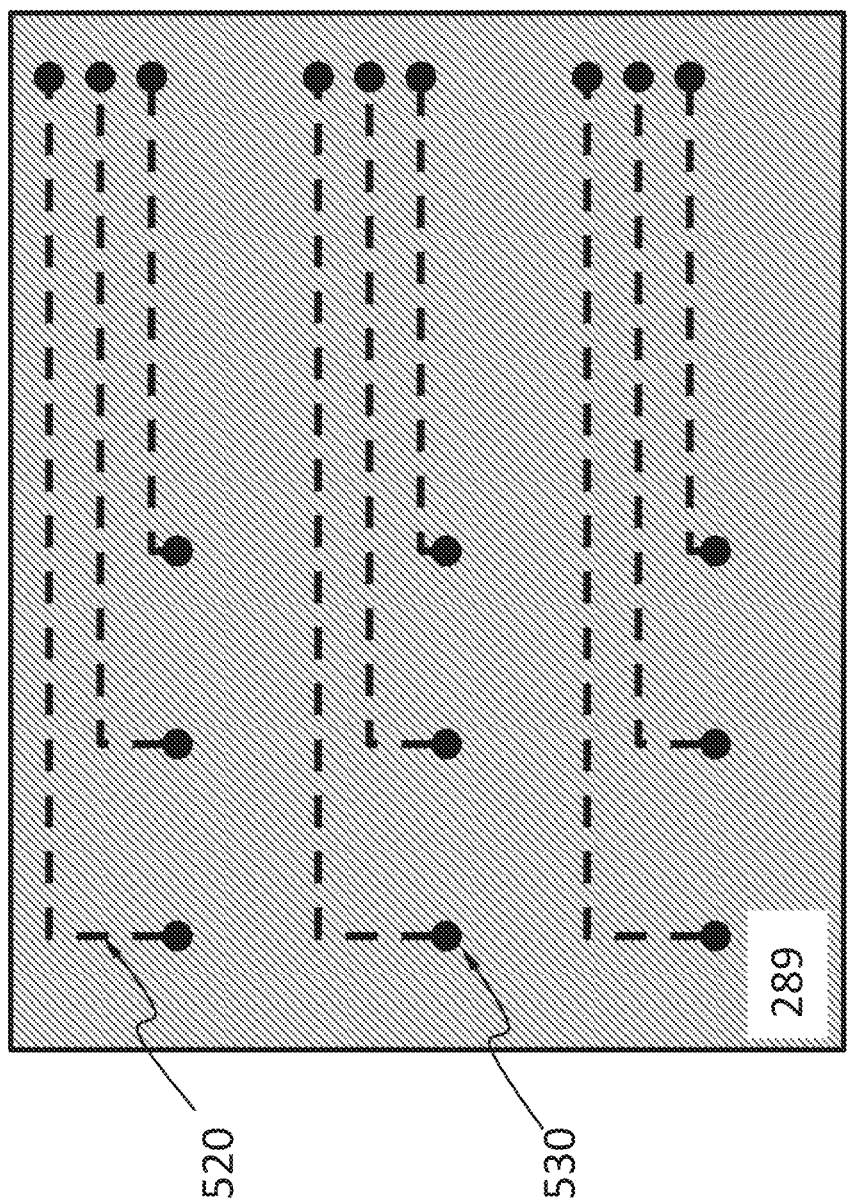
FIG. 8C schematically shows a bottom view of the optical system in FIG. 8A.

FIG. 8B shows a top view of the sensor 251 in FIG. 8A to illustrate the positions of the vias 510 relative to the pixels 270 and the control circuit 271. The pixels 270 and the control circuit 271 are shown in dotted lines because they are not directly visible in this view. FIG. 8C shows a bottom view of the optical system 285 in FIG. 8A to illustrate the positions of the vias 530 relative to the transmission lines 520 (shown as dotted lines because they are not directly visible in this view).

Figure 9A:
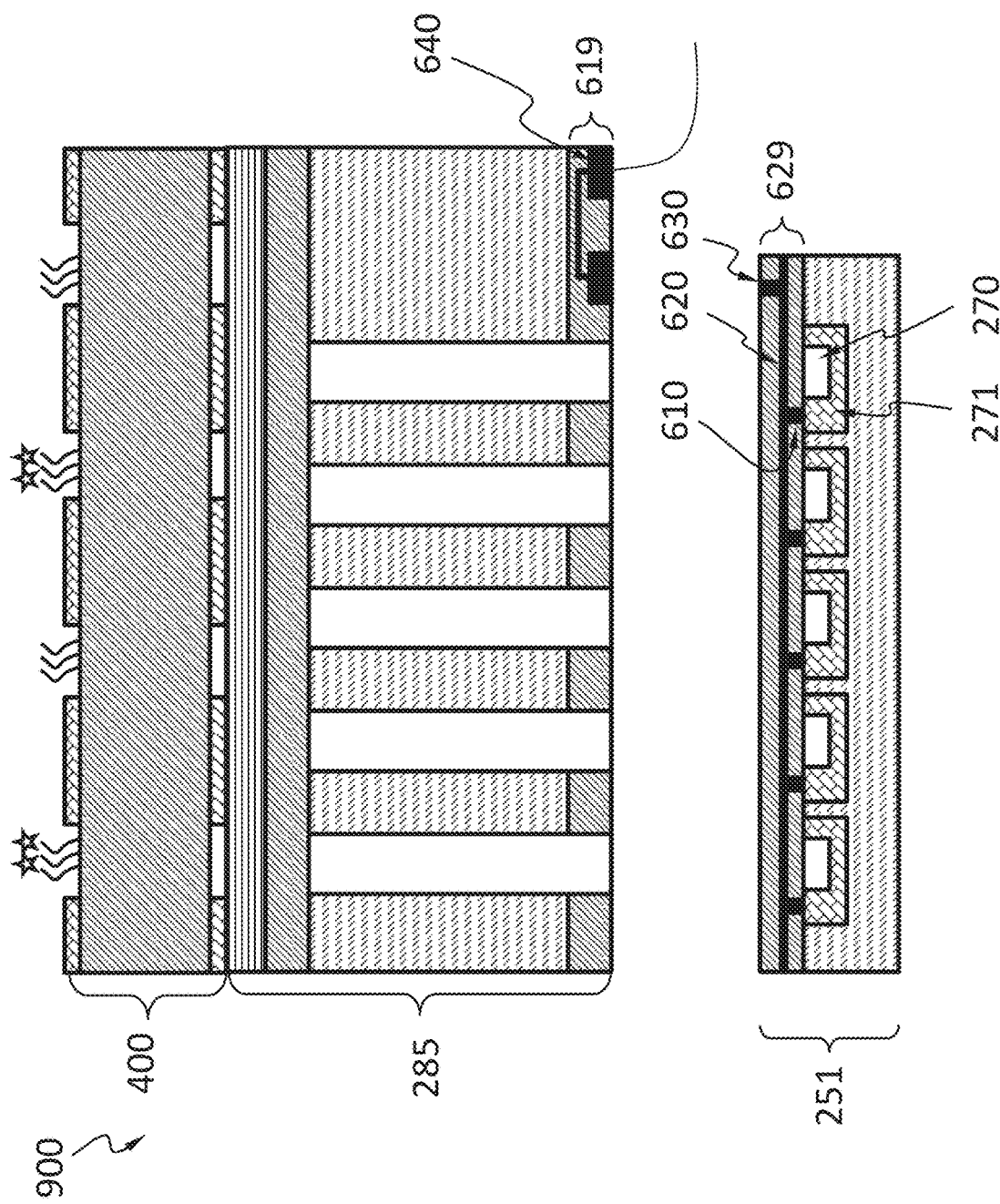
FIG. 9A schematically shows an apparatus wherein a sensor in a microarray may have a redistribution layer and that the optical system in the microarray may have a signal transfer layer, according to an embodiment.

In an embodiment, schematically shown in FIG. 9A, in apparatus 900, the sensor 251 has a redistribution layer 629. The redistribution layer 629 may have a plurality of vias 610 and a plurality of transmission lines 620. The redistribution layer 629 may have electrically insulation materials (e.g., silicon oxide) around the vias 610 and the transmission lines 620. The vias 610 electrically connect the control circuit 271 to the transmission lines 620. The optical system 285 may have a layer 619 with bonding pads 640. The redistribution layer 629 may also have vias 630 electrically connecting the transmission lines 620 to the bonding pads 640, when the sensor 251 and the optical system 285 are bonded. The bonding pads 640 may have two parts connected by a wire buried in the layer 619. This configuration shown in FIG.

10A allows the bonding pads 640 to be positioned on an opposite side from the probe carrier.

Figure 9B:
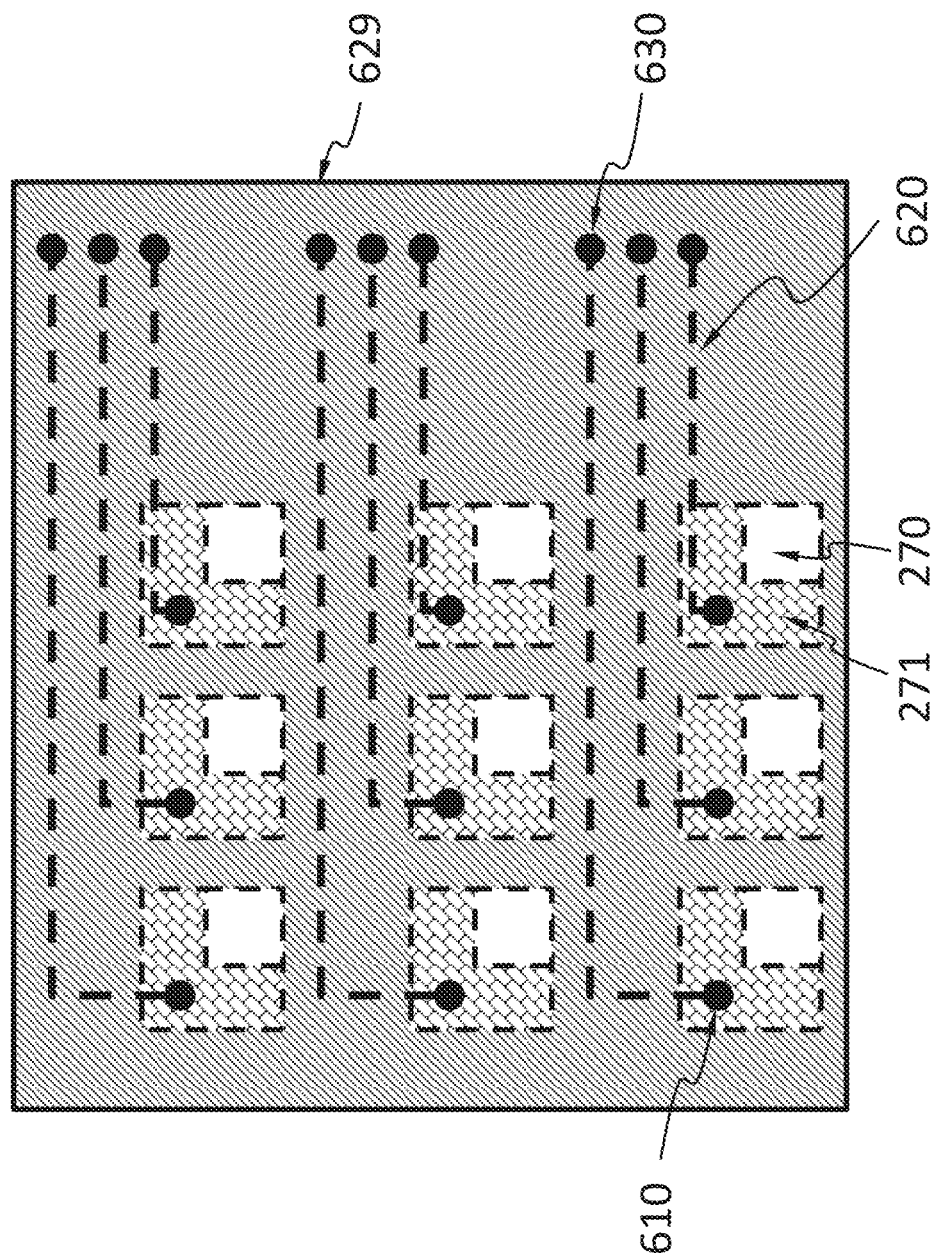
FIG. 9B schematically shows a top view of the sensor in FIG. 9A, according to an embodiment.
Figure 9C:
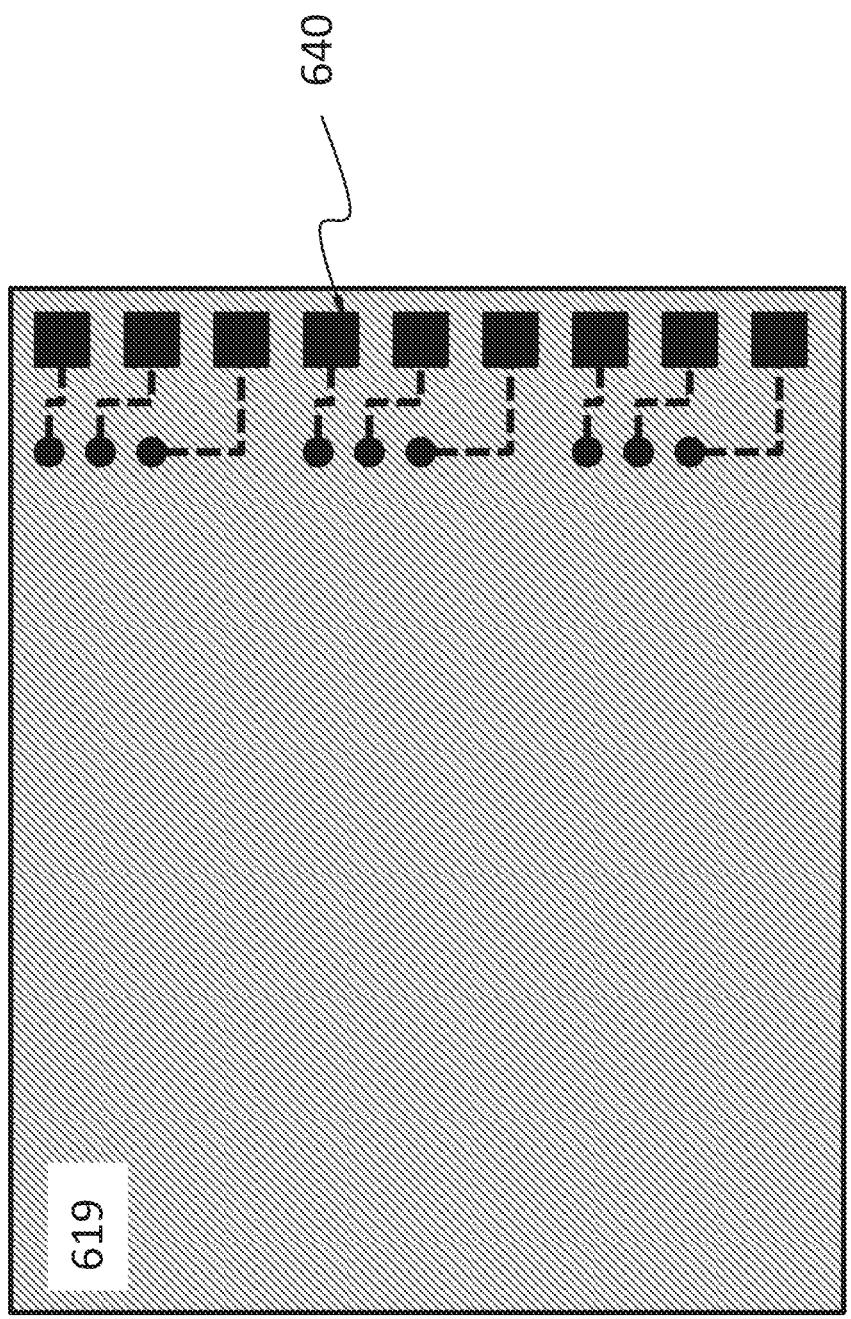
FIG. 9C schematically shows a bottom view of the optical system in FIG. 9A, according to an embodiment.

FIG. 9B shows a top view of the sensor 251 in FIG. 9A to illustrate the positions of the vias 610, the vias 630 and the transmission lines 620, relative to the pixels 270 and the control circuit 271, according to an embodiment. The pixels 270, the control circuit 271 and the transmission lines 620 are shown in dotted lines because they are not directly visible in this view. FIG. 9C shows a bottom view of the optical system 285 in FIG. 9A to illustrate the positions of the bonding pads 640, which are positioned to connect to the vias 630 shown in FIG. 9B. The bonding pads 640 may have two parts connected by a wire buried in the layer 619.

Figure 9D:
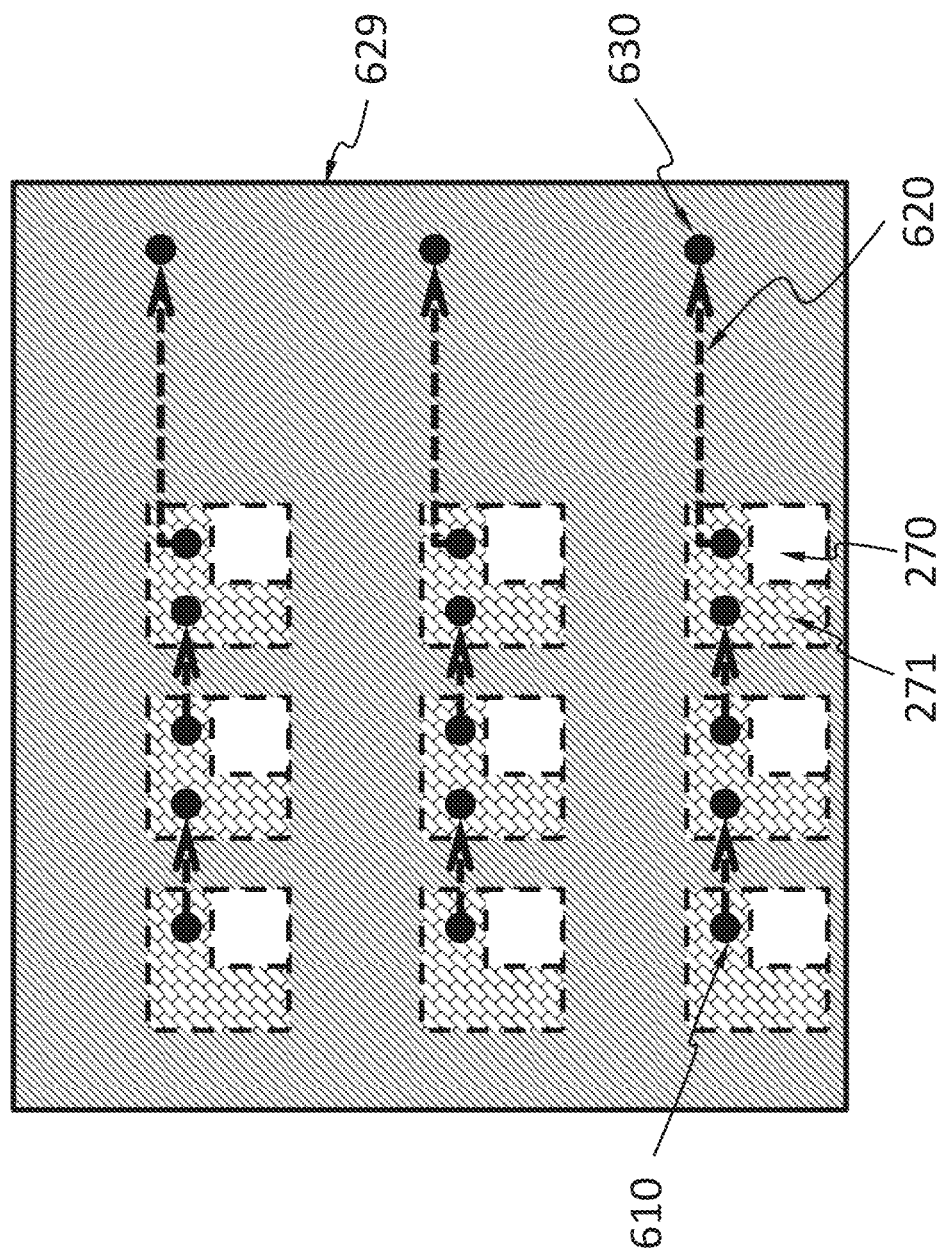
FIG. 9D schematically shows a top view of the sensor in FIG. 9A, according to an embodiment.
Figure 9E:
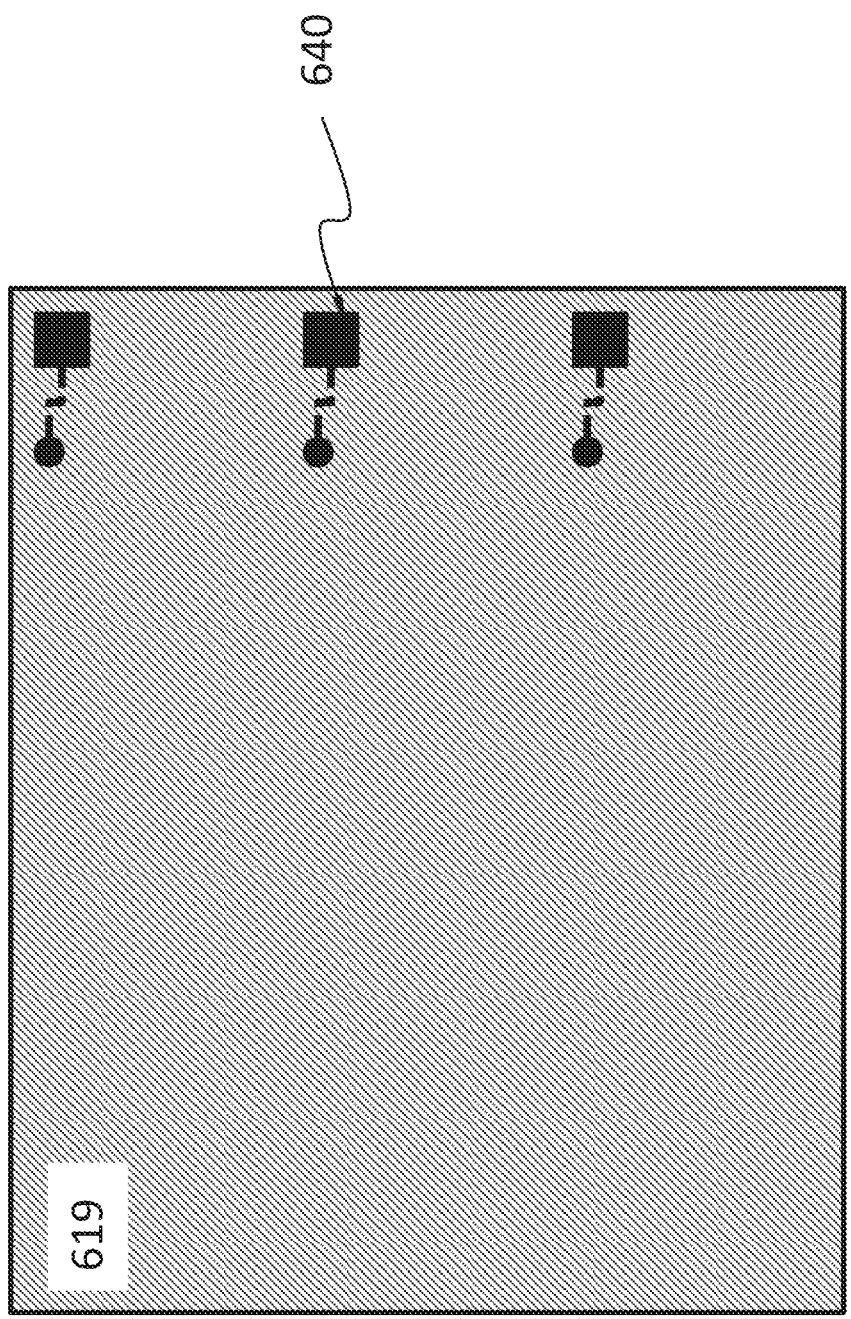
FIG. 9E schematically shows a bottom view of the optical system in FIG. 9A to illustrate the positions of the bonding pads, which are positioned to connect to the vias shown in FIG. 10D.

FIG. 9D shows a top view of the sensor 251 in FIG. 9A to illustrate the positions of the vias 610, the vias 630 and the transmission lines 620, relative to the pixels 270 and the control circuit 271, according to an embodiment. The pixels 270, the control circuit 271 and the transmission lines 620 are shown in dotted lines because they are not directly visible in this view. The pixels 270 may be read out column by column. For example, signal from one 270 may be stored in register in the control circuit 271 associated with that pixel 270; the signal may be successively shifted from one column to the next, and eventually to other processing circuitry through vias 630. FIG. 9E shows a bottom view of the optical system 285 in FIG. 9A to illustrate the positions of the bonding pads 640, which are positioned to connect to the vias 630 shown in FIG. 9D. The bonding pads 640 may have two parts connected by a wire buried in the layer 619.

Figure 9F:
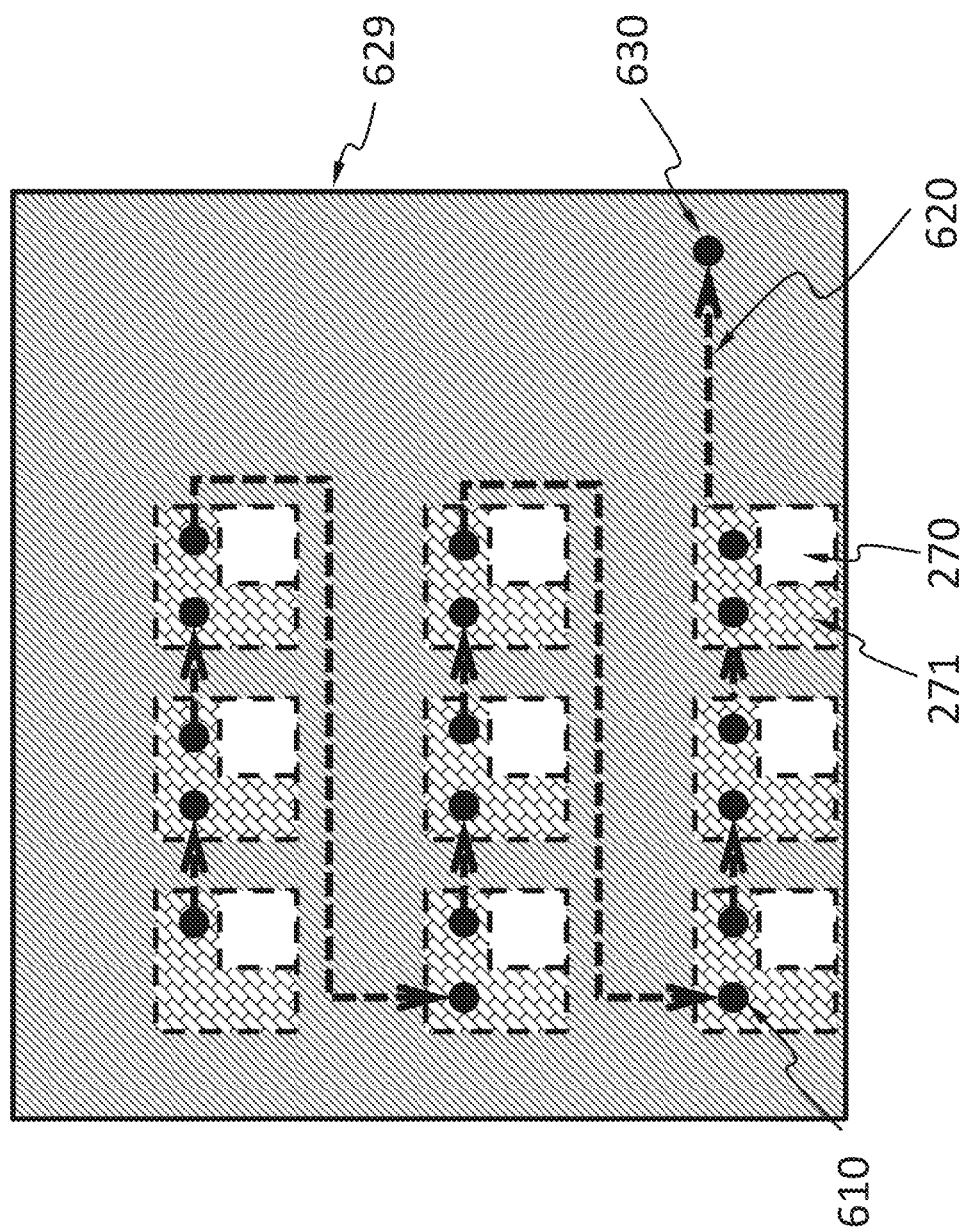
FIG. 9F schematically shows a top view of the sensor in FIG. 9A, according to an embodiment.
Figure 9G:
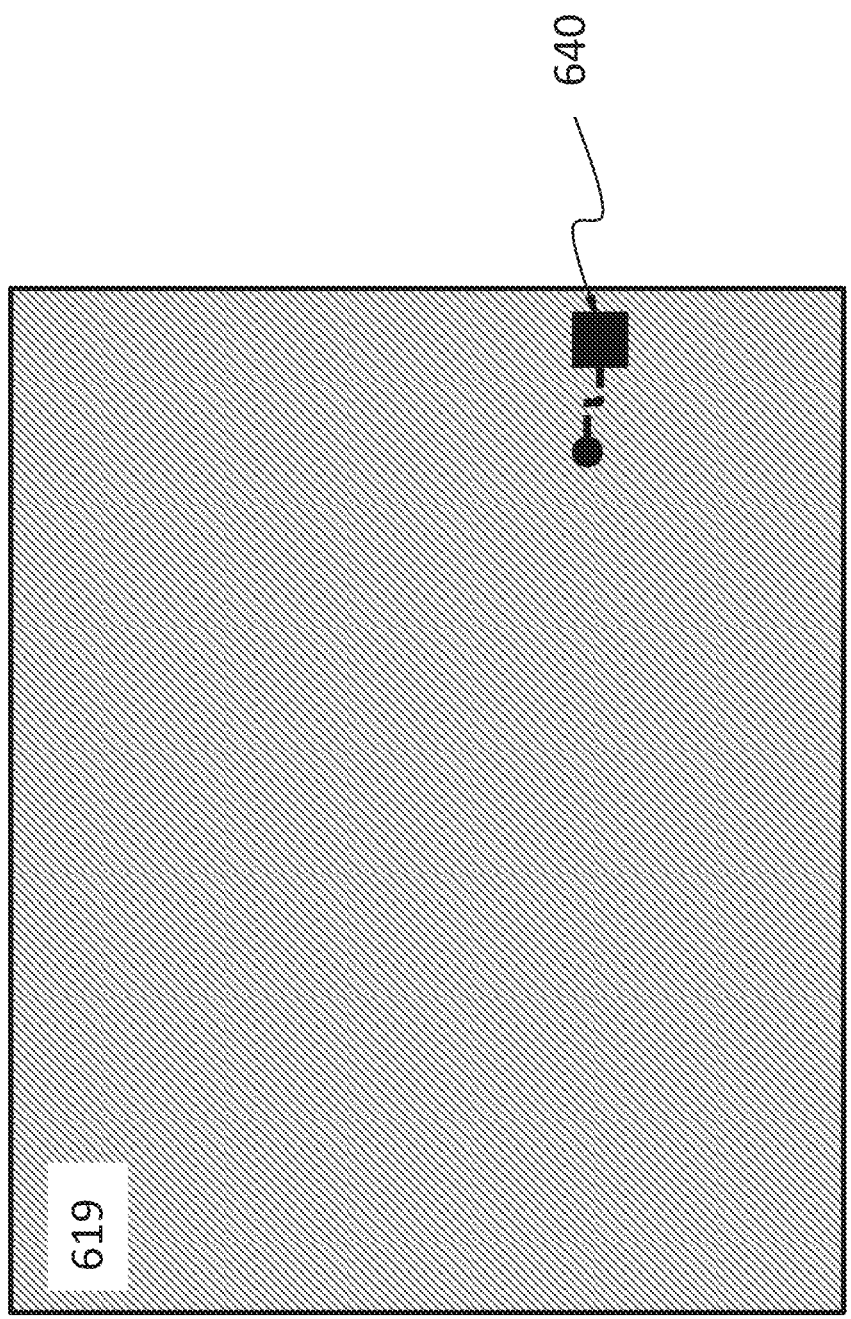
FIG. 9G schematically shows a bottom view of the optical system in FIG. 9A to illustrate the positions of the bonding pad, which are positioned to connect to the via shown in FIG. 9F.

FIG. 9F shows a top view of the sensor 251 in FIG. 9A to illustrate the positions of the vias 610, the via 630 and the transmission lines 620, relative to the pixels 270 and the control circuit 271, according to an embodiment. The pixels 270, the control circuit 271 and the transmission lines 620 are shown in dotted lines because they are not directly visible in this view. The pixels 270 may be read out pixel by pixel. For example, signal from one 270 may be stored in register in the control circuit 271 associated with that pixel 270; the signal may be successively shifted from one pixel to the next, and eventually to other processing circuitry through via 630. FIG. 9G shows a bottom view of the optical system 285 in FIG. 9A to illustrate the positions of the bonding pad 640, which are positioned to connect to the via 630 shown in FIG. 9F. The bonding pads 640 may have two parts connected by a wire buried in the layer 619.

Figure 10:
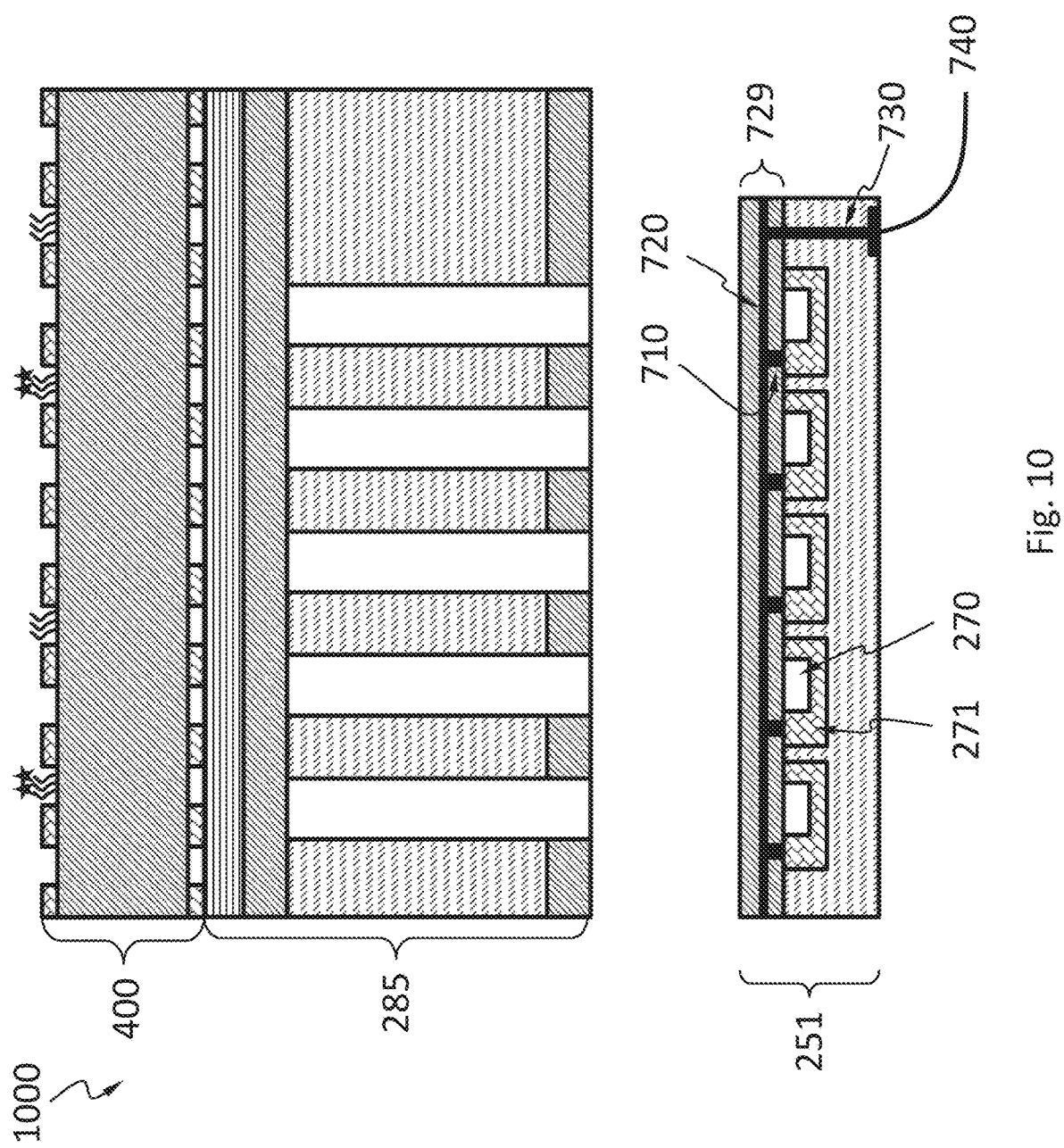
FIG. 10 schematically shows that system wherein a sensor in a microarray may have a redistribution layer with vias such as through-silicon vias (TSV) configured to electrically connect the transmission lines in the redistribution layer to bonding pads on the side opposite from the redistribution layer, according to an embodiment.

In an embodiment, schematically shown in FIG. 10, in apparatus 1000, the sensor 251 has a redistribution layer 729. The redistribution layer 729 may have a plurality of vias 710 and a plurality of transmission lines 720. The redistribution layer 729 may have electrically insulation materials (e.g., silicon oxide) around the vias 710 and the transmission lines 720. The vias 710 electrically connect the control circuit 271 to the transmission lines 720. The redistribution layer 729 may also have vias 730 (e.g., through-silicon vias (TSV)) electrically connecting the transmission lines 720 to bonding pads 740 on the side opposite from the redistribution layer 729. This configuration shown in FIG. 10 allows the bonding pads 740 to be positioned on an opposite side from the probe carrier.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus, comprising:
a probe carrier, an optical system and a sensor;
wherein the probe carrier comprises a substrate, a first layer and a second layer;
wherein the substrate comprises a first surface, a second surface, one or more locations on the first surface configured to be deposit sites for one or more probes;
wherein the second surface is at an opposite side of the substrate from the first surface;
wherein the first layer is on the first surface of the substrate or is embedded in the substrate under the first surface;
wherein the second layer is on the second surface of the substrate or is embedded in the substrate under the second surface;
wherein when signals are generated by the one or more probes under excitation of an excitation radiation, the first layer and the second layer are each configured to attenuate a reflective portion of the signals;
wherein the first layer does not coincide with the one or more locations;
wherein the second layer comprises one or more windows, each of which is aligned with one of the one or more locations to allow pass-through of the signals from the one location.

2. The apparatus of claim 1, wherein the substrate comprises silicon or glass.

3. The apparatus of claim 1, wherein the first layer comprises a roughened surface.

4. The apparatus of claim 1, wherein the first layer comprises a first absorbent material sublayer configured to absorb a transmissive portion of the signals generated from the one or more probes.

5. The apparatus of claim 4, wherein the first absorbent material sublayer comprises a broad spectrum absorbent material or a narrow band absorbent material.

6. The apparatus of claim 1, wherein the first layer comprises a first coupling material sublayer configured to reduce internal reflection of the signal in the substrate.

7. The apparatus of claim 6, wherein the first coupling material sublayer is a single-layer interference type consisting of a single quarter-wave layer of transparent material whose refractive index is about the square root of the substrate's refractive index.

8. The apparatus of claim 6, wherein the first coupling material sublayer is a multi-layer interference type anti-reflection coating comprising alternating layers of a low-index material and a higher-index material, or wherein first coupling material sublayer is an absorbing anti-reflection coating.

9. The apparatus of claim 1, wherein the first layer comprises a blocking material sublayer configured to block at least a portion of the excitation radiation.

10. The apparatus of claim 1, wherein the second layer comprises a second absorbent material sublayer configured to absorb a reflective portion of the signal generated from the probe.

11. The apparatus of claim 10, wherein the second absorbent material sublayer comprises a broad spectrum absorbent material or a narrow band absorbent material.

12. The apparatus of claim 1, wherein the second layer comprises a second coupling material sublayer configured to reduce internal reflection of the signal in the substrate.

13. The apparatus of claim 12, wherein the second coupling material sublayer is a single-layer interference type consisting of a single quarter-wave layer of transparent material whose refractive index is about the square root of the substrate's refractive index.

14. The apparatus of claim 12, wherein the second coupling material sublayer is multi-layer interference type comprising alternating layers of a low refractive index material and a higher refractive index material.

15. The apparatus of claim 1, wherein the sensor comprises a plurality of pixels configured to detect the signals generated by the one or more probes under excitation of the excitation radiation.

16. The apparatus of claim 15, wherein the sensor comprises a control circuit configured to control, acquire data from, or process data from the pixels.

17. The apparatus of claim 15, wherein the pixels are optically coupled to the locations by the optical system.

18. The apparatus of claim 15, wherein the pixels are arranged in an array and are configured to be read out column by column.

19. The apparatus of claim 15, wherein the pixels are arranged in an array and are configured to be read out pixel by pixel.

20. The apparatus of claim 1, wherein the signal is luminescence.

21. The apparatus of claim 1, wherein the optical system comprises a filter.

22. The apparatus of claim 21, wherein the filter is configured to block at least a portion of the excitation radiation.

23. The apparatus of claim 21, wherein the filter is a dichroic filter.

24. The apparatus of claim 21, wherein the filter comprises a meta-material, quantum dots or a photonic crystal.

25. The apparatus of claim 1, wherein the optical system comprises a transmissive layer.

26. The apparatus of claim 1, wherein the optical system comprises a plurality of microlens.

27. The apparatus of claim 1, wherein the optical system comprises a plurality of collimators.

28. The apparatus of claim 27, wherein the collimators comprise a meta-material, quantum dots or a photonic crystal.

29. The apparatus of claim 27, wherein the collimators are configured to eliminate optical cross-talk between neighboring pixels among the plurality of pixels.

30. The apparatus of claim 27, wherein at least one of the collimators comprises a core and a sidewall surrounding the core.

31. The apparatus of claim 30, wherein the core is a material that essentially prevents the excitation radiation from passing through irrespective of propagation direction of the excitation radiation.

32. The apparatus of claim 30, wherein the core comprises a dichroic filter.

33. The apparatus of claim 30, wherein the core allows the signal to pass through essentially unabsorbed.

34. The apparatus of claim 30, wherein the core is a void space.

35. The apparatus of claim 30, wherein the sidewall attenuates a portion of the signal reaching the sidewall.

36. The apparatus of claim 30, wherein the sidewall is textured.

* * * * *